(12) United States Patent
Kawata

(10) Patent No.: US 11,846,737 B2
(45) Date of Patent: Dec. 19, 2023

(54) DATA PROCESSING APPARATUS, DATA PROCESSING METHOD, AND NON-TRANSITORY COMPUTER-READABLE STORAGE MEDIUM FOR STORING DATA PROCESSING PROGRAM

(71) Applicant: CANON MEDICAL SYSTEMS CORPORATION, Otawara (JP)

(72) Inventor: Go Kawata, Nagareyama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/663,250

(22) Filed: May 13, 2022

(65) Prior Publication Data
US 2022/0381928 A1 Dec. 1, 2022

(30) Foreign Application Priority Data
Jun. 1, 2021 (JP) .................... 2021-092061

(51) Int. Cl.
*G01T 1/208* (2006.01)
*G01T 1/22* (2006.01)
*G01T 1/20* (2006.01)
*G01T 1/29* (2006.01)
*G01T 1/16* (2006.01)
*G01T 1/24* (2006.01)
*G01T 1/36* (2006.01)
(Continued)

(52) U.S. Cl.
CPC ............... *G01T 1/208* (2013.01); *A61B 6/037* (2013.01); *A61B 6/586* (2013.01); *G01N 23/20066* (2013.01); *G01T 1/1603* (2013.01); *G01T 1/172* (2013.01); *G01T 1/20181* (2020.05); *G01T 1/20184* (2020.05); *G01T 1/22* (2013.01); *G01T 1/242* (2013.01); *G01T 1/247* (2013.01); *G01T 1/248* (2013.01); *G01T 1/249* (2013.01); *G01T 1/2985* (2013.01); *G01T 1/363* (2013.01)

(58) Field of Classification Search
CPC .. G01T 1/208; G01T 1/20181; G01T 1/20184; G01T 1/22; G01T 1/242; G01T 1/247; G01T 1/248; G01T 1/249; G01T 1/2985; G01T 1/172; G01T 1/363; G01T 1/1603; A61B 6/037; A61B 6/586
See application file for complete search history.

(56) References Cited

U.S. PATENT DOCUMENTS

2011/0095173 A1* 4/2011 Menge .................... G01T 1/208
250/362
2019/0324161 A1* 10/2019 Ota ........................ G01T 1/2985
(Continued)

FOREIGN PATENT DOCUMENTS

EP    3 614 181 A1    2/2020
JP    2020-516889 A   6/2020

*Primary Examiner* — David P Porta
*Assistant Examiner* — Casey Bryant
(74) *Attorney, Agent, or Firm* — Oblon, McClelland, Maier & Neustadt, L.L.P.

(57) ABSTRACT

A data processing apparatus according to an embodiment includes acquisition circuitry and specification circuitry. The acquisition circuitry is configured to acquire a detector signal containing a first component that is based on Cherenkov light and a second component that is based on scintillation light. The specification circuitry is configured to specify timing information about generation of the detector signal by curve fitting to the first component.

8 Claims, 15 Drawing Sheets

(51) Int. Cl.
   *A61B 6/03*      (2006.01)
   *G01T 1/172*     (2006.01)
   *A61B 6/00*      (2006.01)
   *G01N 23/20066*  (2018.01)

(56) References Cited

U.S. PATENT DOCUMENTS

2022/0065803 A1* 3/2022 Kawata ................. A61B 6/4258
2022/0196856 A1* 6/2022 Kawata ................. G01T 1/2002

* cited by examiner

AREA OF PULSES (SUM AFTER AD CONVERSION, ETC.)→OBSERVATION ENERGY

≈SCINTILATOR IMPARTED ENERGY $E_{dep}$

OBSERVATION γ-RAY ENERGY≈SCINTILATOR IMPARTED ENERGY $E_{dep}$

DATA PROCESSING APPARATUS, DATA PROCESSING METHOD, AND NON-TRANSITORY COMPUTER-READABLE STORAGE MEDIUM FOR STORING DATA PROCESSING PROGRAM

CROSS-REFERENCE TO RELATED APPLICATIONS

This application is based upon and claims the benefit of priority from Japanese Patent Application No. 2021-092061, filed on Jun. 1, 2021; the entire contents of which are incorporated herein by reference.

FIELD

Embodiments described herein relate generally to a data processing apparatus, a data processing method, and a non-transitory computer-readable storage medium for storing a data processing program.

BACKGROUND

When time-resolved measuring is carried out using a detector signal like a positron emission tomography (PET) apparatus, etc., a rise-up may be slowed depending on a signal band. The slowed rise-up delays a timing when waveform of the detector signal crosses a threshold depending on intensity of the output signal. This leads to a deteriorated result of estimation on the real event occurrence time. A deteriorated result of estimation on an event occurrence time is referred to as trigger-time-walk. Variation in the trigger-time-walk often causes a problem in quality of a PET image produced by a PET apparatus. A conventional PET apparatus calibrates relation between the intensity of the detector signal and the trigger-time-walk, in advance. In detecting gamma rays, the PET apparatus then corrects an event occurrence time concerning detection of the gamma rays using the calibration. This requires a time-to-digital converter (TDC) with a high time resolution. The TDC with a high time resolution may increase costs.

In a conventional PET apparatus, gain indicating relation between detector signal and radiation energy usually has variation. Because of the variation in gain, the relation between the trigger-time-walk and the energy varies in each detector. Due to this, the complicated calibration as described above needs to be performed for the entire of detectors, which requires a lot of time and efforts. In addition, correction of an event occurrence time may be performed using a trained model, such as a trained neural network. This requires pre-training and the pre-training requires a large amount of memory capacity.

DETAILED DESCRIPTION

A data processing apparatus explained in an embodiment below includes acquisition circuitry and specification circuitry. The acquisition circuitry acquires a detector signal containing a first component that is based on Cherenkov light and a second component that is based on scintillation light. The specification circuitry specifies timing information about generation of the detector signal by curve fitting to the first component.

Embodiments of the data processing apparatus, a data processing method, and a non-transitory computer-readable storage medium for storing a data processing program will be explained below with reference to the accompanying drawings. In the following embodiments, parts denoted with the same referential numeral or sign perform the same operation, and thus redundant explanation will not be repeated. For concrete explanation, it is assumed that the data processing apparatus according to an embodiment is included in a time-of-flight (TOF) positron emission tomography apparatus (hereinafter, "Cherenkov TOFPET apparatus") that can detect Cherenkov light and uses a time-of-flight difference between a pair of annihilation radiations for image reconstruction. The Cherenkov light is produced through inelastic-scattering with electrons in a light emitter, accompanied by the electrons moving faster than a phase velocity of light in the light emitter. Radiation of the Cherenkov light is completed in a short time, for example, in 1 ns or less after its emission in the light emitter.

The data processing apparatus herein is an equivalent of a data acquisition system (DAS) in the Cherenkov TOFPET apparatus. The data collecting apparatus may be included in another radiation diagnosis apparatus capable of detecting Cherenkov light. The radiation herein is a gamma ray, for example. Note that the radiation is not limited to a gamma ray, and it may be any radiation that can generate Cherenkov light. For convenience of explanation, the structure and processing procedure of the data processing apparatus is described below first, followed by a Cherenkov TOFPET apparatus including this data processing apparatus.

First Embodiment

Figure 1:
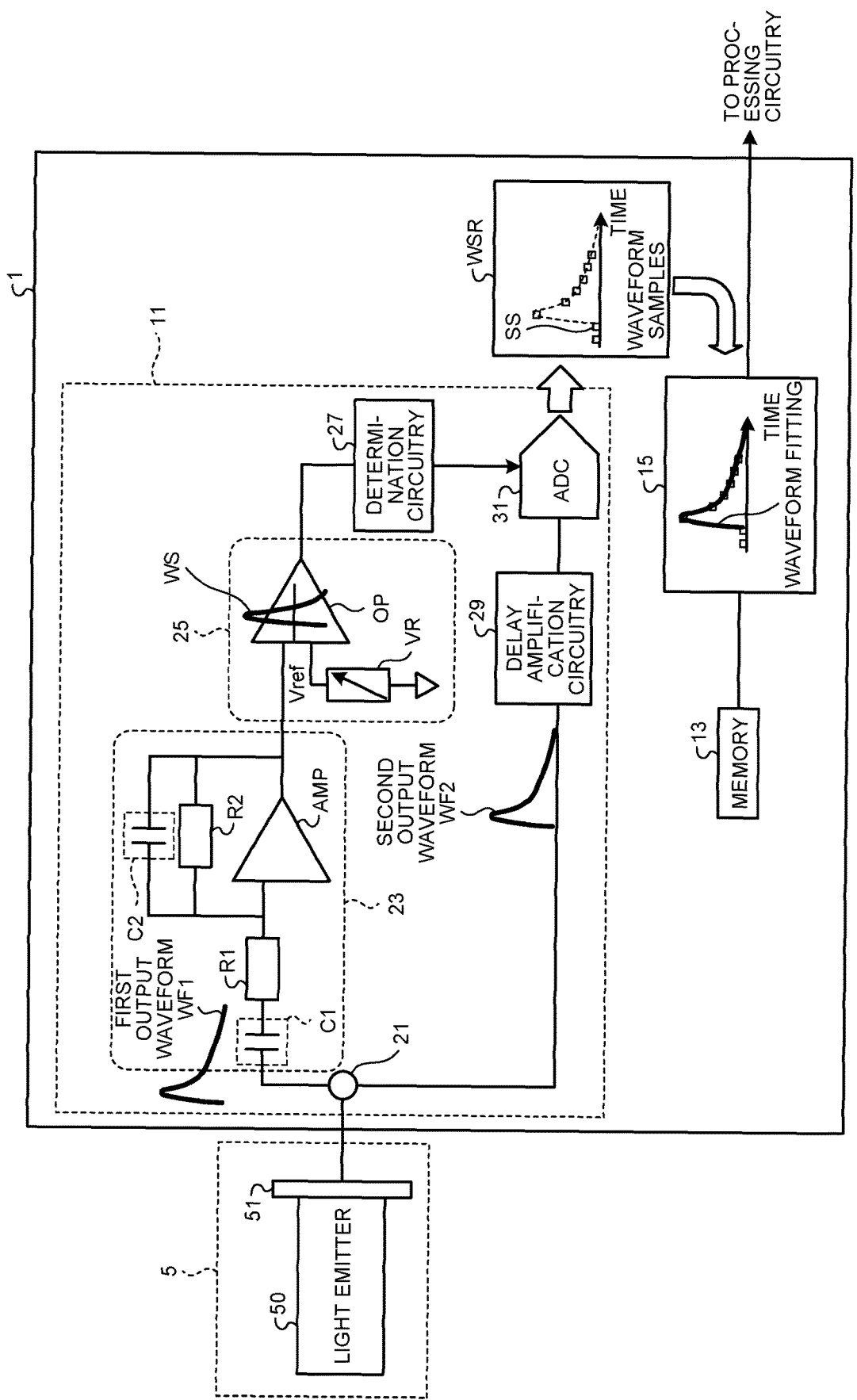
FIG. 1 is a schematic diagram illustrating an example of structure of a data processing apparatus according to a first embodiment of the present invention.

FIG. 1 is a schematic diagram illustrating an example of structure of a data processing apparatus 1 according to a first embodiment of the present invention. As illustrated in FIG. 1, the data processing apparatus 1 includes an acquisition unit 11, a memory 13, and specification circuitry 15. The acquisition unit 11 is implemented by acquisition circuitry that includes a divider 21, a waveform shaping circuitry 23, a comparator 25, a determination circuitry 27, a delay amplification circuitry 29, and a converter 31 corresponding to an analog-to-digital converter (hereinafter, "ADC"). An input terminal of the divider 21 of the data processing apparatus 1 is electrically coupled to, for example, a light sensor 51 of a detector 5. An output terminal of the specification circuitry 15 of the data processing apparatus 1 is electrically coupled to processing circuitry of a Cherenkov TOFPET apparatus.

The detector 5 includes a light emitter 50 and the light sensor 51. The light emitter 50 is implemented by a scintillator, for example. The scintillator can be made of, for example, a medium with which scintillation light is difficult to produce, the medium including for example bismuth germanium oxide (BGO), cadmium tungstate oxide (CdWO$_4$), and lead compounds such as lead glass (SiO$_2$+PbO), lead fluoride (PbF$_2$), or PWO (PbWO$_4$). In addition to the above medium with which scintillation light is difficult to produce, the scintillator may be implemented by two-layered structure of scintillator crystal suitable for TOF measuring and energy measuring, such as lanthanum bromide (LaBr$_3$), lutetium yttrium oxyorthosilicate (LYSO), lutetium oxyorthosilicate (LSO), lutetium gadolinium oxyorthosilicate (LGSO), etc., or BGO. The light emitter is not limited to scintillators, and the light emitter may be a radiator that radiates light in response to incidence of gamma rays.

The light sensor 51 detects light produced by the light emitter 50. The light sensor 51 corresponds to a silicon photomultiplier (SiPM) or a photoelectron amplifier, for example, and the light sensor 51 may be implemented by an avalanche photodiode (hereinafter, "APD"), for example. Note that the light sensor 51 is not limited to a SiPM or a photoelectron amplifier, and the light sensor 51 may be implemented by any other light receiving sensor capable of detecting light.

The divider 21 divides an output waveform that is output from the light sensor 51 into a first output waveform WF1 and a second output waveform WF2. The output waveform corresponds to a detector signal containing a first component that is based on Cherenkov light and a second component that is based on scintillation light. An existing circuit structure is available for circuit structure of the divider 21, and its explanation is omitted. As illustrated in FIG. 1, among diversions of the detector signal, the first output waveform WF1 is output to the waveform shaping circuitry 23. Among diversions of the detector signal, the second output waveform WF2 is output to the delay amplification circuitry 29.

The waveform shaping circuitry 23 shapes the waveform of the first output waveform WF1 by, for example, adjusting frequency characteristics of the first output waveform WF1 and providing the first output waveform WF1 with gain and offset. Note that the waveform shaping circuitry 23 may remove noises in the first output waveform WF1. The waveform shaping circuitry 23 outputs the shaped first output waveform (hereinafter, "shaped waveform WS") to the comparator 25. Circuit structure of the waveform shaping circuitry 23 includes, for example as illustrated in FIG. 1, an amplifier AMP, a resistor R1 and a capacitor C1 electrically serial-coupled to the amplifier AMP, and a resistor R2 and a capacitor C2 electrically serial-parallel-coupled to the amplifier AMP. Note that the circuit structure of the waveform shaping circuitry 23 is not limited to the circuit structure as illustrated in FIG. 1, and it may be implemented by another circuit structure.

The comparator 25 compares the shaped waveform WS to a predetermined threshold (corresponding to a voltage Vref). As illustrated in FIG. 1, the comparator 25 includes an operational amplifier OP and a variable resistor VR, for example. Note that circuit structure of the comparator 25 is not limited to the circuit structure as illustrated in FIG. 1, and it may be implemented by another circuit structure. The operational amplifier OP compares the shaped waveform WS to the voltage Vref output from the variable VR. The comparator 25 thereby outputs a result of comparison between the shaped waveform WS and the threshold voltage Vref to the determination circuitry 27. For example, when the voltage value of the shaped waveform WS is less than the voltage Vref, the result of comparison is a signal value indicative of 0; and when the voltage value of the shaped waveform WS is the voltage Vref or greater, the result of comparison corresponds to a signal value indicative of 1. Note that it is possible to set or adjust the voltage Vref corresponding to the threshold as appropriate by changing resistance of the variable resistor VR.

The determination circuitry 27 determines necessity of sampling of the second output waveform WF2 based on an output from the comparator 25. For example, when receiving a signal value indicative of 0 as an output of the comparator 25, the determination circuitry 27 outputs a signal to the ADC 31 to stop the sampling. In response, the ADC 31 stops operation of sampling signals that are output from the delay amplification circuitry 29. When receiving a signal value indicative of 1 as an output from the comparator 25, the determination circuitry 27 outputs a signal to the ADC 31 to execute sampling. In response, the ADC 31 starts operation to sample signals that are output from the delay amplification circuitry 29. In other words, the determination circuitry 27 controls operation of the ADC 31 in accordance with the signal output from the comparator 25. The determination circuitry 27 corresponds to a determination unit.

The delay amplification circuitry 29 provides the second output waveform WF2 with predetermined delay and predetermined amplification. The predetermined delay is, for example, a time interval at least one sampling time longer than a time interval between when the first output waveform WF1 is input to the waveform shaping circuitry 23 and when the ADC 31 starts operating by the determination circuitry 27. The predetermined amplification corresponds to an amplification factor to amplitude of the second output waveform WF2. The predetermined amplification and the predetermined delay can be set as appropriate.

The ADC 31 converts the amplified and delayed second output waveform WF2 into a digital waveform based on the result of determination by the determination circuitry 27. More particularly, when a value 1 is output from the determination circuitry 27, the ADC 31 performs sampling with respect to the amplified and delayed second output waveform WF2 at a predetermined sampling frequency. Waveform samples WSR represented by a plurality of quadrangulars in FIG. 1 indicate results of sampling with respect to the amplified and delayed second output waveform WF2. Among the waveform samples WSR illustrated as the quadrangulars in FIG. 1, the time of a sample (quadrangular) SS having the earliest time corresponds to a time the predetermined delay earlier than a time when the shaped waveform WS exceeds the threshold Vref. The ADC 31 outputs the waveform samples WSR to the specification circuitry 15. An existing circuit structure is available for circuit structure of the ADC 31, and its explanation is omitted.

The memory 13 is implemented by a semiconductor memory element, such as a random access memory (RAM) or a flash memory. Note that the memory 13 may be a driving apparatus that reads and write various information from and to a semiconductor memory element or the like, such as a RAM. The memory 13 stores therein a control program for controlling various circuitry in the present embodiment.

The memory 13 stores therein a shape of a function (hereinafter, "fitting function") that is curve-fit to the waveform samples WSR, a time constant of the fitting function, and a predetermined threshold. The fitting function is an analytic function indicating temporal change in detector signal (for example, amplitude) caused by Cherenkov light and scintillation light. Note that the memory 13 may store therein a table corresponding to the fitting function. The fitting function, for example, describes an output waveform from the light sensor 51 accompanied by detection of gamma rays as an analytical solution by convolution of a result of analysis obtained as a physical average of a probability process concerning generation of scintillation light and generation of Cherenkov light and an equivalent circuit of a transfer function by an indirect detector (the light sensor 51), such as an APD. The fitting function herein has the amplitude (crest value) of detector signal and the timing information about generation of the detector signal as parameters concerning curve fitting. The timing information is, more particularly, times relating to generation of scintillation light and generation of Cherenkov light, in other words, a time when gamma rays arrive at the light emitter 50. The fitting function may further have a parameter about a contribution of the Cherenkov light to the detector signal.

An exemplary fitting function F (A, $t_0$;t) is described by expression (1) as follow:

$$F(A, t_0; t) = A \cdot f(t - t_0) \quad (1)$$

$$= A \cdot \left( \exp\left(-\frac{t-t_0}{\tau_1}\right) - \exp\left(-\frac{t-t_0}{\tau_2}\right) + \beta\left(\exp\left(-\frac{t-t_0}{\tau_3}\right) - \exp\left(-\frac{t-t_0}{\tau_4}\right)\right) \right) \text{ for } t \geq 0$$

where A in expression (1) corresponds to the amplitude of the fitting function, $t_0$ in expression (1) corresponds to the timing information, and t in expression (1) corresponds to a time later than the arrival time of the gamma rays.

The first term inside the parentheses of the right side of expression (1) is represented by the following expression:

$$\exp\left(-\frac{t-t_0}{\tau_1}\right) - \exp\left(-\frac{t-t_0}{\tau_2}\right)$$

where $\tau_1$ and $\tau_2$ in the above expression correspond to time constants concerning attenuation of amplitude of the second component (output from the light sensor 51 due to the scintillation light), for example. The time constants $\tau_1$ and $\tau_2$ are acquired experimentally, for example.

The second term inside the parentheses of the right side of expression (1) is represented by the following expression:

$$\beta\left(\exp\left(-\frac{t-t_0}{\tau_3}\right) - \exp\left(-\frac{t-t_0}{\tau_4}\right)\right)$$

where $\tau_3$ and $\tau_4$ in the above expression correspond to time constants concerning the first component (output from the light sensor 51 due to the Cherenkov light), for example. The time constants $\tau_3$ and $\tau_4$ are acquired experimentally, for example. Parameter β in the above expression corresponds to the parameter concerning the contribution of the Cherenkov light to the detector signal. This parameter may be pre-set.

Note that the fitting function is not limited to expression (1), and it may be described by expression (2) as follow:

$$F(A, t_0; t) = A \cdot f(t - t_0) = A \cdot \exp\left(-\frac{(t-t_0)^2}{B}\right) \quad (2)$$

Expression (2) above corresponds to Gaussian, where B in expression (2) corresponds to a time constant concerning the first component and the second component. In other words, B in expression (2) corresponds to a time constant concerning the Cherenkov light and the scintillation light.

Figure 4:
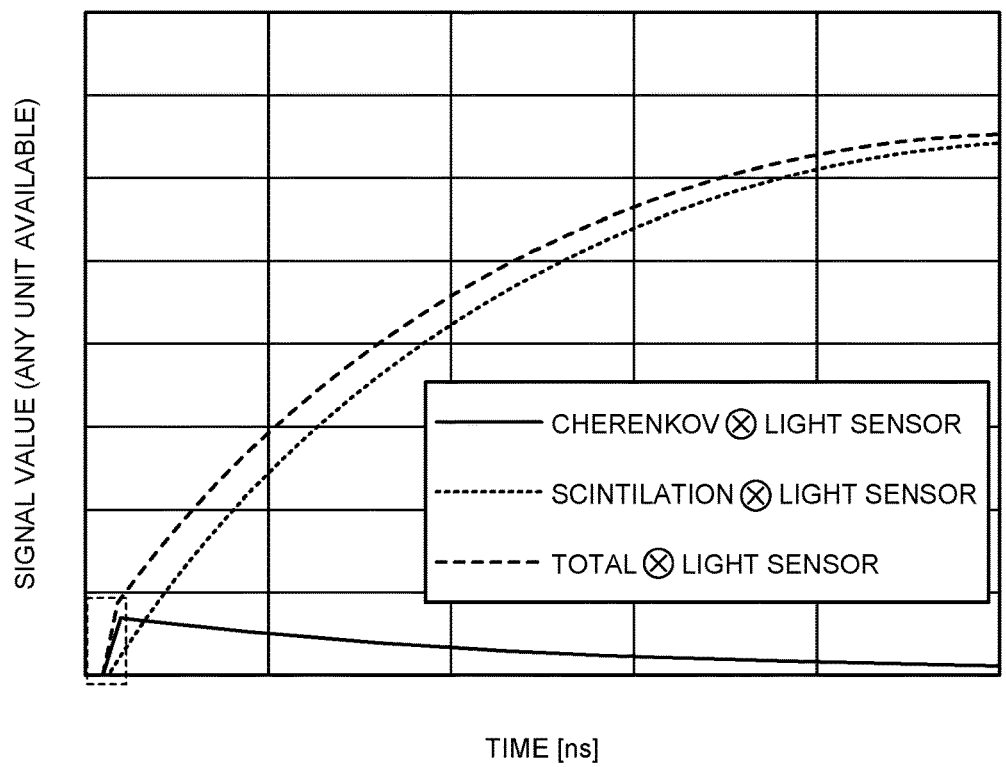
FIG. 4 is a diagram illustrating an example of temporal change in a fitting function that is curve-fit to a waveform sample.

The specification circuitry 15 specifies timing information about generation of detector signal by curve-fitting to the first component in the waveform samples WSR. For example, the specification circuitry 15 specifies, as timing information, an arrival time ($t_0$ in expression (1)) when gamma rays from which the Cherenkov light is generated arrive at the detector 5 within a period (first component) indicated by a dotted-line frame as illustrated in FIG. 4 in which the Cherenkov light is dominant in the output signal. More particularly, the specification circuitry 15 further specifies the amplitude of the detector signal, i.e., the energy of the gamma rays (A in expression (1)) by curve fitting using the fitting function. Note that the specification circuitry 15 may specify parameter β, which relates to the contribution of the Cherenkov light to the detector signal, by the curve fitting. Moreover, the specification circuitry 15 may specify the timing information, the amplitude of detector signal, and the contribution of the Cherenkov light to the detector signal by curve fitting to the first component and to the second component.

More particularly, the specification circuitry 15 reads the fitting function from the memory 13. The specification circuitry 15 then performs curve fitting to the sampled digital waveform (waveform samples WS) using expression (1). The specification circuitry 15 specifies, by the curve fitting to the digital waveform, the timing information about generation of the output waveform (arrival time when the gamma rays arrive at the detector 5). The specification circuitry 15 further specifies the energy of the gamma rays and the contribution of the Cherenkov light to the detector signal ($\beta$ in expression (1)). The specification circuitry 15 corresponds to a specification unit.

Note that the determination circuitry 27, the specification circuitry 15, etc., may be implemented as processing circuitry. The processing circuitry herein has a function (determination function) executed by the determination circuitry 27 and a function (specification function) executed by the specification circuitry 15. The processing circuitry implementing the determination function and the specification function corresponds to a determination unit and a specification unit, respectively. Note that the specification function may be executed after a plurality of waveform samples is stored in the memory 13, for example, when the data processing apparatus 1 is offlined from the light sensor 51, in other words, on non-real-time basis in view of gamma-ray detection. In this case, the waveform samples WS are stored in the memory 13.

The determination circuitry 27 and the specification circuitry 15 include, as hardware resources, a processor such as a CPU and a micro processing unit (MPU) and a memory such as a read only memory (ROM) and a random access memory (RAM). The determination circuitry 27 and the specification circuitry 15 may be implemented by an application specific integrated circuit (ASIC), a field programmable gate array (FPGA), a complex programmable logic device (CPLD), or a simple programmable logic device (SPLD).

Figure 2:
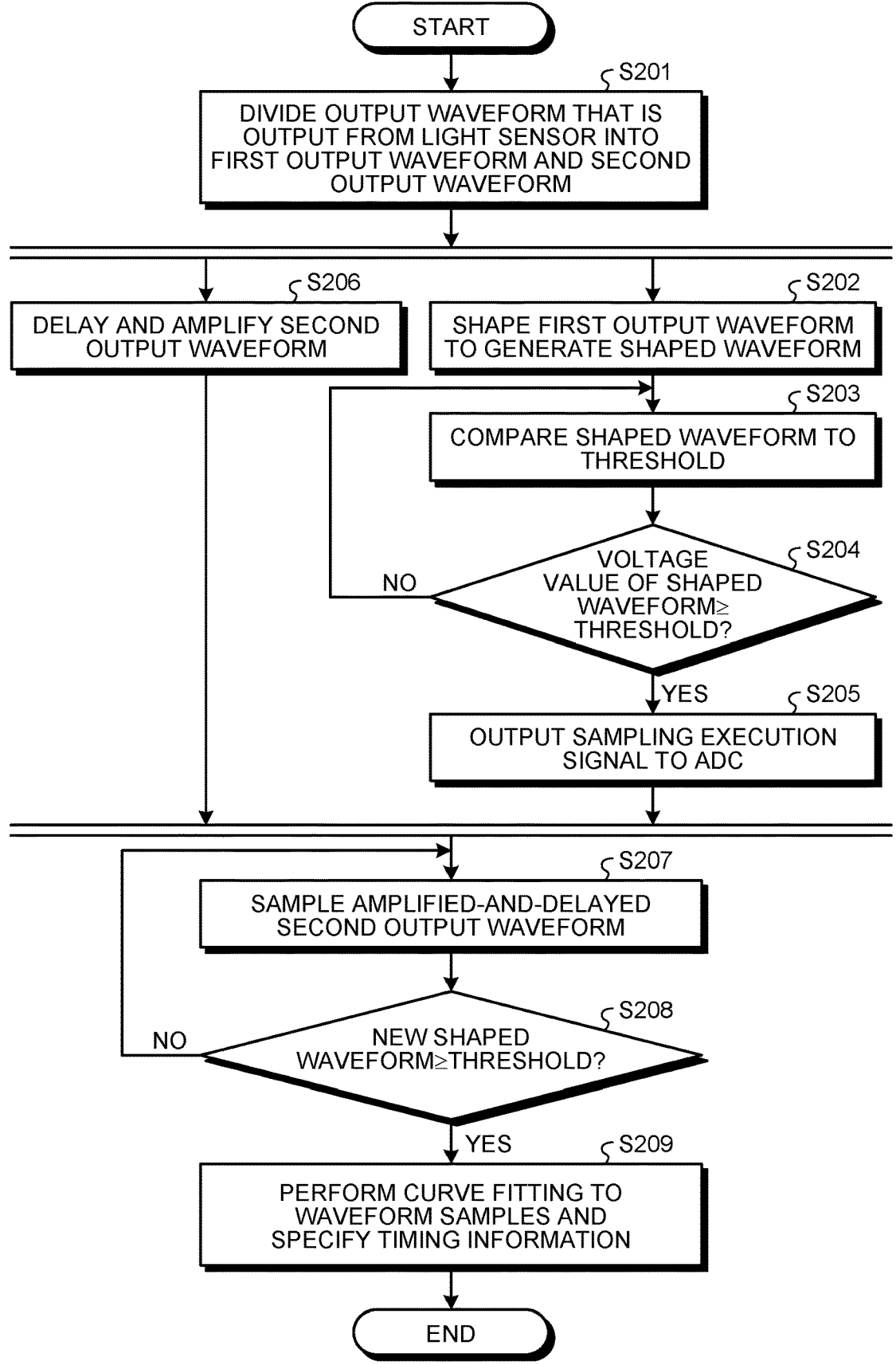
FIG. 2 is a flowchart of an example of procedure of a timing acquiring process according to the first embodiment.

The structure of the data processing apparatus 1 is explained above. Explained below is a process of acquiring the timing information (hereinafter, "timing acquiring process"). FIG. 2 is a flowchart of an example of procedure of the timing acquiring process.

Timing Acquiring Process

Step S201

When gamma rays enter the light emitter 50, the light emitter 50 generates scintillation light and Cherenkov light. The light sensor 51 detects the scintillation light and the Cherenkov light. The light sensor 51 outputs a detector signal containing a first component that is based on the Cherenkov light and a second component that is based on the scintillation light as an output waveform to the divider 21. The divider 21 divides the output waveform that is output from the light sensor 51 into the first output waveform WF1 and the second output waveform WF2. The first output waveform WF1 is output to the waveform shaping circuitry 23. The second output waveform WF2 is output to the delay amplification circuitry 29.

Step S202

The waveform shaping circuitry 23 shapes the first output waveform WF1 to generate the shaped waveform WS. The shaped waveform WS is output to the comparator 25.

Step S203

The comparator 25 compares a voltage value of the shaped waveform WS to the threshold Vref. Note that the threshold Vref may be adjusted and set as appropriate before execution of the timing acquiring process. The comparator 25 outputs a result of comparison to the determination circuitry 27.

Step S204

When the voltage value of the shaped waveform WS is equal to or greater than the threshold Vref (Yes at Step S204), a process at Step S205 is performed. When the voltage value of the shaped waveform WS is less than the threshold Vref (No at Step S204), the process at Step S203 is performed.

Step S205

Upon receiving a signal value indicative of 1 as the result of comparison, the determination circuitry 27 outputs a sampling execution signal to the ADC 31.

Step S206

The delay amplification circuitry 29 provides the second output waveform WF2 with predetermined delay and predetermined amplification. The delayed and amplified second output waveform WF2 is output to the ADC 31.

Step S207

The ADC 31 samples the amplified and delayed second output waveform WF2. The ADC 31 thus generates the waveform samples WSR. The waveform samples WSR are output to the specification circuitry 15. Note that if the curve fitting by the specification circuitry 15 is performed offline, the ADC 31 outputs the waveform samples WSR to the memory 13. In this case, the waveform samples WSR are stored in the memory 13.

Step S208

When a new shaped waveform that is input to the comparator 25 is equal or greater than the threshold Vref (Yes at Step S208), a process at Step S209 is performed. In this case, for the new shaped waveform, the processes at Step S205 and the subsequent steps are performed. When a new shaped waveform that is input to the comparator 25 is less than the threshold Vref (No at Step S208), the process at Step S207 is repeated Step S209

The specification circuitry 15 reads the fitting function (expression (1)) from the memory 13. The specification circuitry 15 performs curve fitting to the waveform samples WSR by the fitting function. More particularly, the specification circuitry 15 performs curve fitting between the waveform samples WSR and the fitting function using a least-square method or a maximum likelihood estimation method. Note that the method of performing curve fitting is not limited to a least-square method or a maximum likelihood estimation method, and it is allowable to use, for example, a trained model such as a pre-trained convolution neural network.

The specification circuitry 15 specifies values of the multiple parameters in expression (1) by the above-mentioned curve fitting. More particularly, the specification circuitry 15 specifies multiple parameter values: the timing information (arrival time $t_0$ when the gamma rays arrive at the detector 5), the amplitude of the detector signal, i.e., the energy of the gamma rays (A in expression (1)), and the contribution of the Cherenkov light to the detector signal ($\beta$ in expression (1)). The specification circuitry 15 outputs the specified values of the multiple parameters to the processing circuitry of the Cherenkov TOFPET apparatus, or the like. The timing acquiring process accompanied by incidence of the gamma rays onto the light emitter 50 is thus completed.

Figure 3:
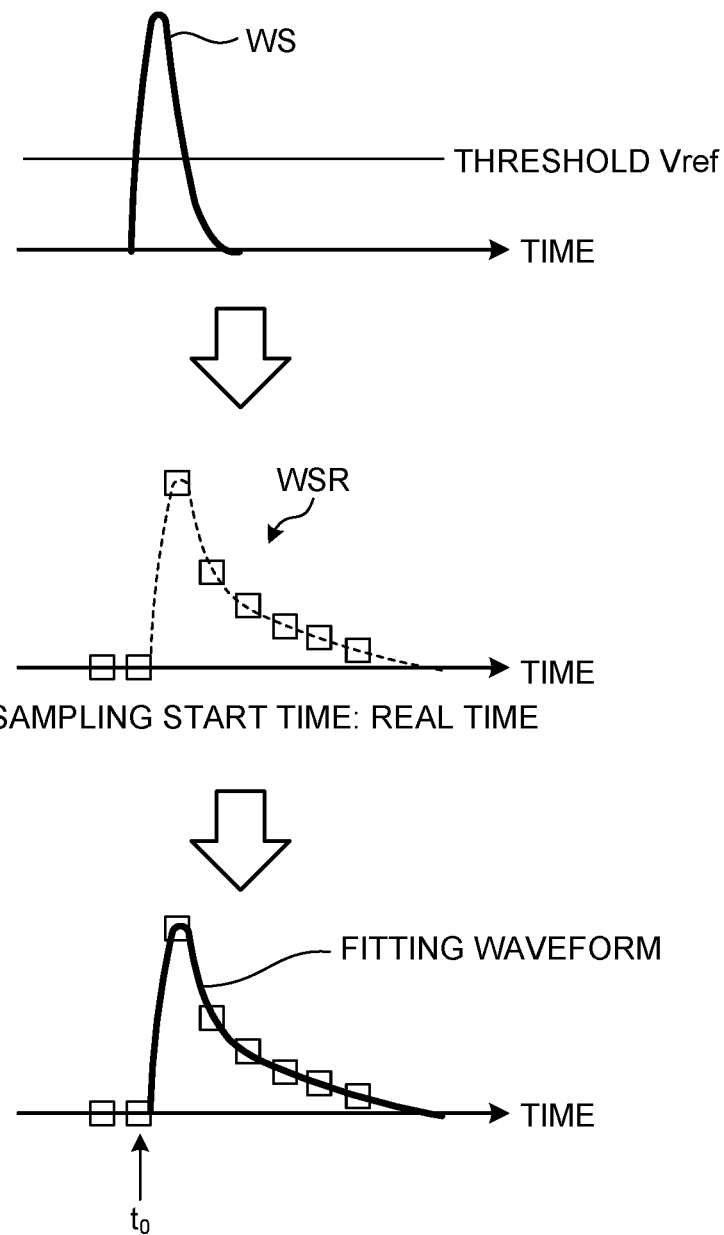
FIG. 3 is a diagram for illustrating an example of curve fitting to a second output waveform delayed and amplified according to the first embodiment.

FIG. 3 is a diagram for illustrating an example of curve fitting to the delayed and amplified second output waveform WF2. As illustrated in FIG. 3, when the shaped waveform WS exceeds the threshold, sampling is performed for the delayed and amplified second output waveform WF2; thereby, the waveform samples WSR are generated. The fitting function (hereinafter, "fitting waveform") that has been curve-fit to the waveform samples WSR is decided by curve-fitting of the fitting function to the waveform samples WSR. The timing information is specified by the fitting waveform. The timing information of FIG. 3 corresponds to $t_0$ in the waveform fitting.

FIG. 4 is a graph illustrating an example of temporal change in the fitting waveform. The temporal change in the fitting waveform as illustrated in FIG. 4 corresponds to what is obtained by convoluting the transfer function concerning the light sensor 51 to at least one of the output due to the scintillation light and the output due to the Cherenkov light. As illustrated in FIG. 4, as for response to an output signal in response to gamma rays incident onto the light emitter 50, the solid-line fitting waveform corresponding to the first component derived from the Cherenkov light responds faster than the dotted-line fitting waveform corresponding to the second component derived from the scintillation light. Due to this, to accurately specify an arrival time when the gamma rays arrive at the light emitter 50, it is important to specify the timing information about generation of the detector signal by curve fitting to the first component of the detector signal (for example, the dotted-line frame in FIG. 4).

Figure 5:
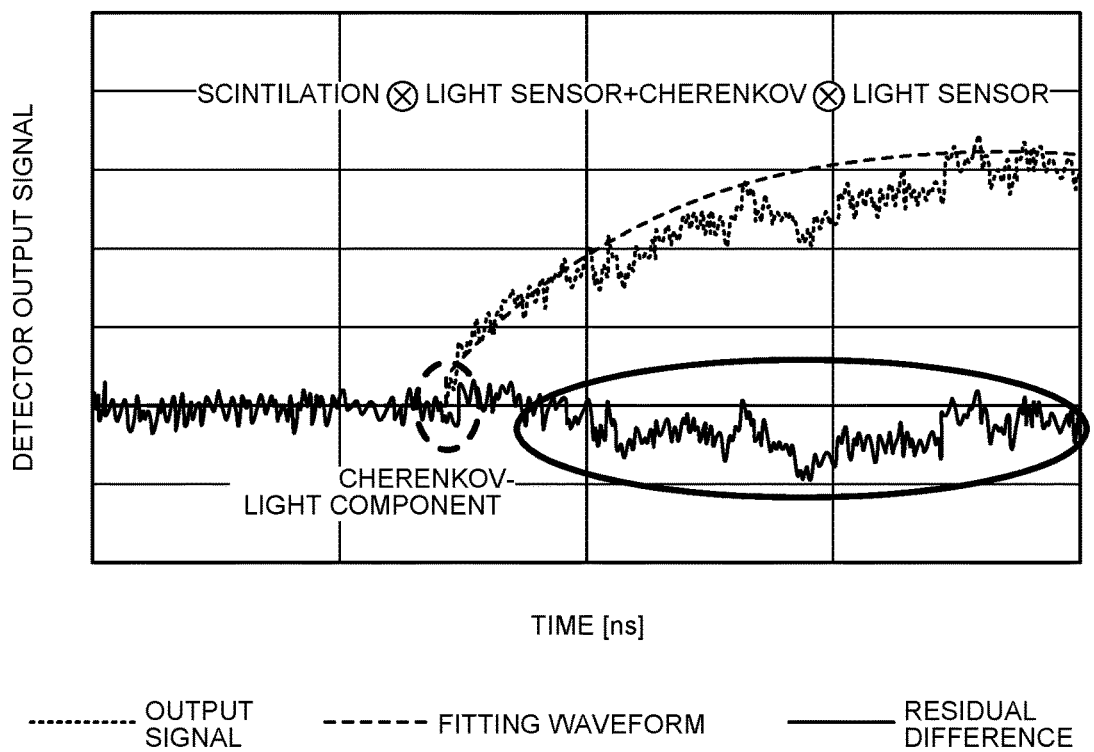
FIG. 5 is a diagram illustrating an example between output signal and fitting waveform according to the first embodiment.

FIG. 5 is a diagram illustrating an example between output signal and fitting waveform. The dashed line in FIG. 5 indicates a residual difference between the output signal indicated by the dotted line and the fitting waveform indicated by the solid line in FIG. 5. As illustrated in FIG. 5, the residual difference is small on or near the rising-up of the output signal. Due to this, in the fitting waveform, curve fitting is performed accurately with the first component (the Cherenkov component) of the output signal. This allows the specification circuitry 15 to specify the timing information with high accuracy from the delayed and amplified second output waveform WF2.

Figure 6:
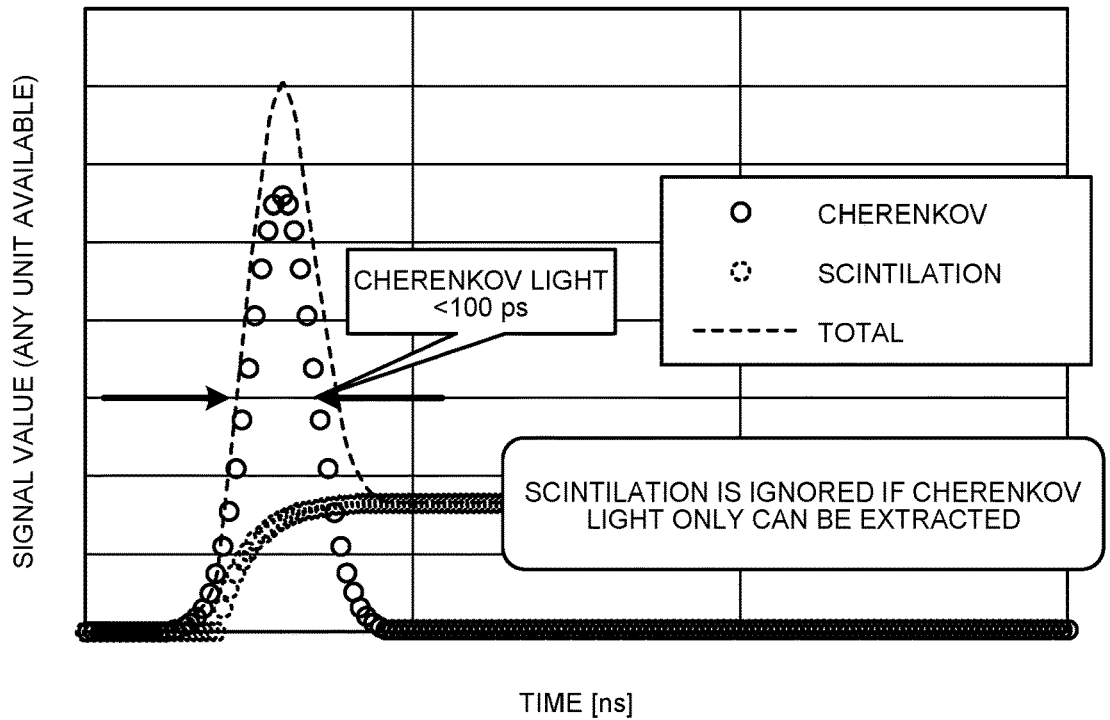
FIG. 6 is a diagram illustrating a time distribution of the number of photons output from a light emitter within a dotted-line frame in FIG. 4.

FIG. 6 is a diagram illustrating a time distribution of the number of photons output from the light emitter 50 within the dotted-line frame in FIG. 4. As illustrated in FIG. 6, on or near the arrival time when the gamma rays arrive at the light emitter 50, the number of photons by the Cherenkov light is, for example, about one digit more than the number of photons by the scintillation light. Therefore, curve fitting to the first component (circular marks in solid lines of FIG. 6) corresponding to the Cherenkov light of the waveform samples WSR reduces fluctuation in the timing information estimated, as compared to the timing information estimated from the scintillation light, and the specification circuitry 15 can specify the timing information with high accuracy. Note that when the first component corresponding to the Cherenkov light is selectively acquired as the output signal depending on the characteristics of the light emitter 50, etc., curve fitting to the second component derived from the scintillation light is ignored.

Figure 7:
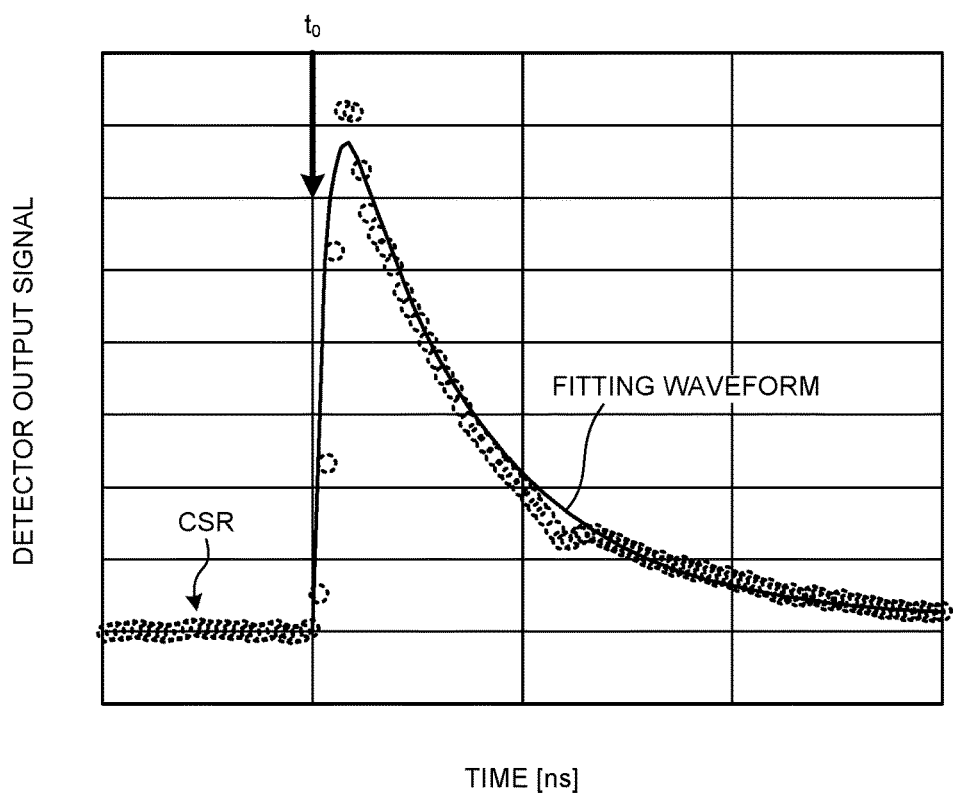
FIG. 7 is a diagram illustrating an example of curve fitting to waveform samples corresponding to Cherenkov light according to the first embodiment.

FIG. 7 is a diagram illustrating an example of curve fitting to waveform samples CSR corresponding to the Cherenkov light. The fitting function herein is in a state where convolution concerning the scintillation light is not performed, in other words, it is in the shape where the first term inside the parentheses of the right side of expression (1) is omitted. As illustrated in FIG. 7, by curve fitting to the waveform samples CSR represented by multiple circular marks in dotted lines, the fitting waveform shows good fitting to the waveform samples CSR. Due to this, the specification circuitry 15 can specify the amplitude (the number of photons) and the timing ($t_0$), which are the parameters of the fitting function corresponding to the Cherenkov light, with high accuracy.

The above-mentioned data processing apparatus 1 according to the first embodiment acquires a detector signal containing a first component that is based on Cherenkov light and a second component that is based on scintillation light and specifies timing information about generation of the detector signal by curve fitting to the first component. For example, this data processing apparatus 1 specifies an arrival time when gamma rays from which the Cherenkov light is generated arrive at the detector 5 as the timing information. More particularly, this data processing apparatus 1 performs the curve fitting using an analytic function indicating temporal change in the detector signal by the Cherenkov light and the scintillation light.

More particularly, this data processing apparatus 1 divides an output waveform output from the light sensor 51 into the first output waveform WF1 and the second output waveform WF2, shapes the first output waveform WF1, compares the shaped first output waveform WS to the predetermined threshold Vref, determines necessity of sampling of the second output waveform WF2 based on an output indicative of a result of comparison, converts the amplified and delayed second output waveform to the digital waveform WSR based on a result of determination on the necessity, and specifies the timing information about generation of the output waveform by curve fitting to the digital waveform WSR.

With this configuration, this data processing apparatus 1 can specify accurate timing information by performing curve fitting to the first component derived from the Cherenkov light, which is more responsive than the second component derived from the scintillation light, by using an analytical solution that has the timing information ($t_0$) indicative of the arrival time when the gamma rays arrive at the detector 5 as a parameter. With this configuration, this data processing apparatus 1 can improve, with a simple manner and low costs, accuracy of estimation of the arrival time when the gamma rays arrive at the detector 5, i.e., the event occurrence time.

Moreover, the data processing apparatus 1 according to the first embodiment specifies parameter β, which relates to the contribution of the Cherenkov light to the detector signal, by curve fitting that uses a fitting function further having parameter β. With this configuration, this data processing apparatus 1 can further improve accuracy of estimation of the arrival time when the gamma rays arrive at the detector 5.

Explained below are effects of the present invention with reference to FIGS. 8 and 9.

Figure 8:
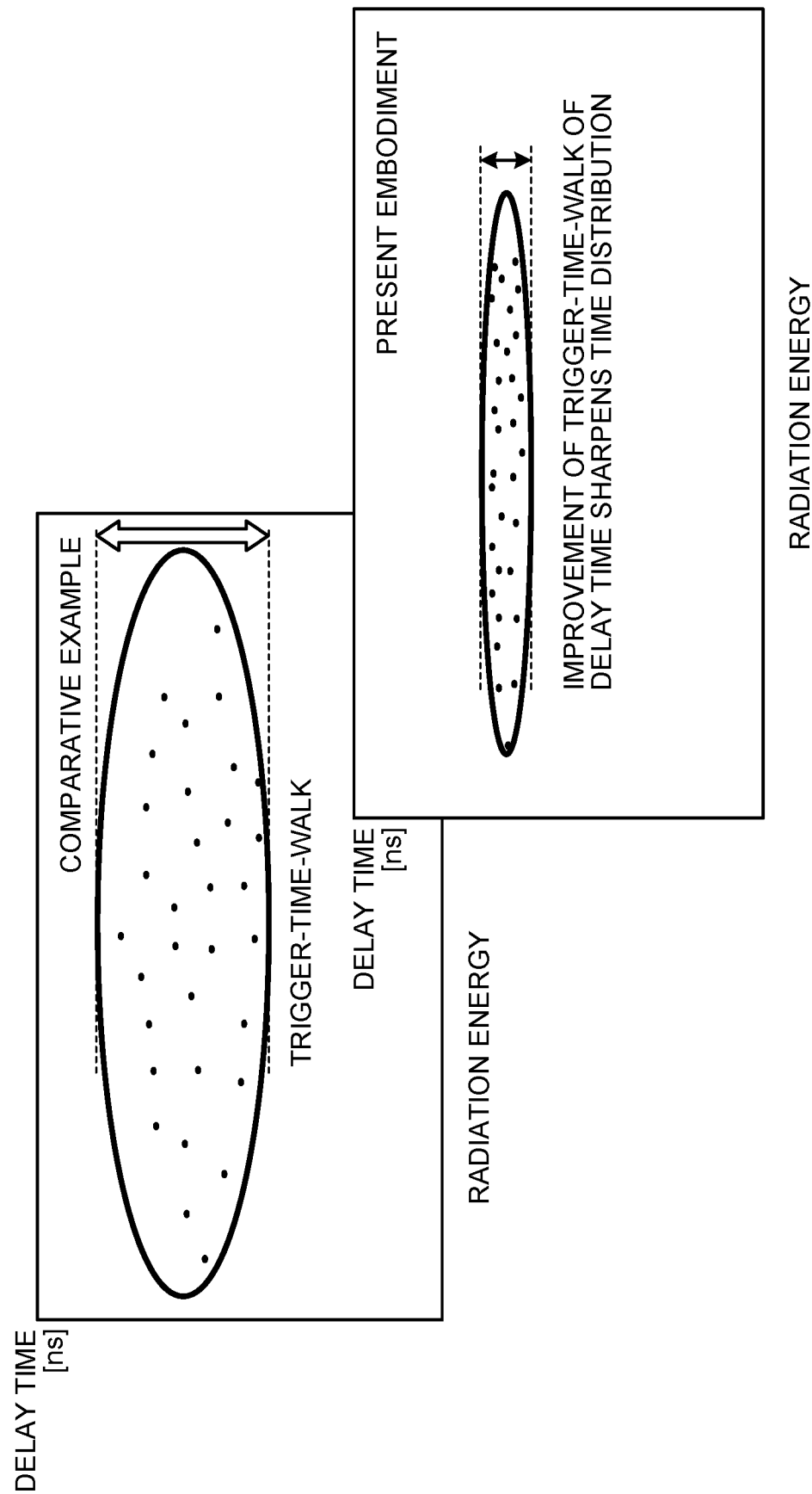
FIG. 8 is a diagram illustrating graphs of delay time (trigger-time-walk) with respect to radiation energy in connection with a comparative example and the first embodiment.

FIG. 8 is a diagram illustrating graphs of delay time (trigger-time-walk) with respect to radiation energy in connection with a comparative example and the present embodiment, the comparative example being an example where no curve fitting is performed. As illustrated in FIG. 8, it is clear that, as for every energy, the width of the delay time according to the present embodiment is narrower than the width of the delay time according to the comparative example. Therefore, the present embodiment can sharpen the time distribution concerning detection of the gamma rays and improve variety in the trigger-time-walk with respect to the energy.

Figure 9:
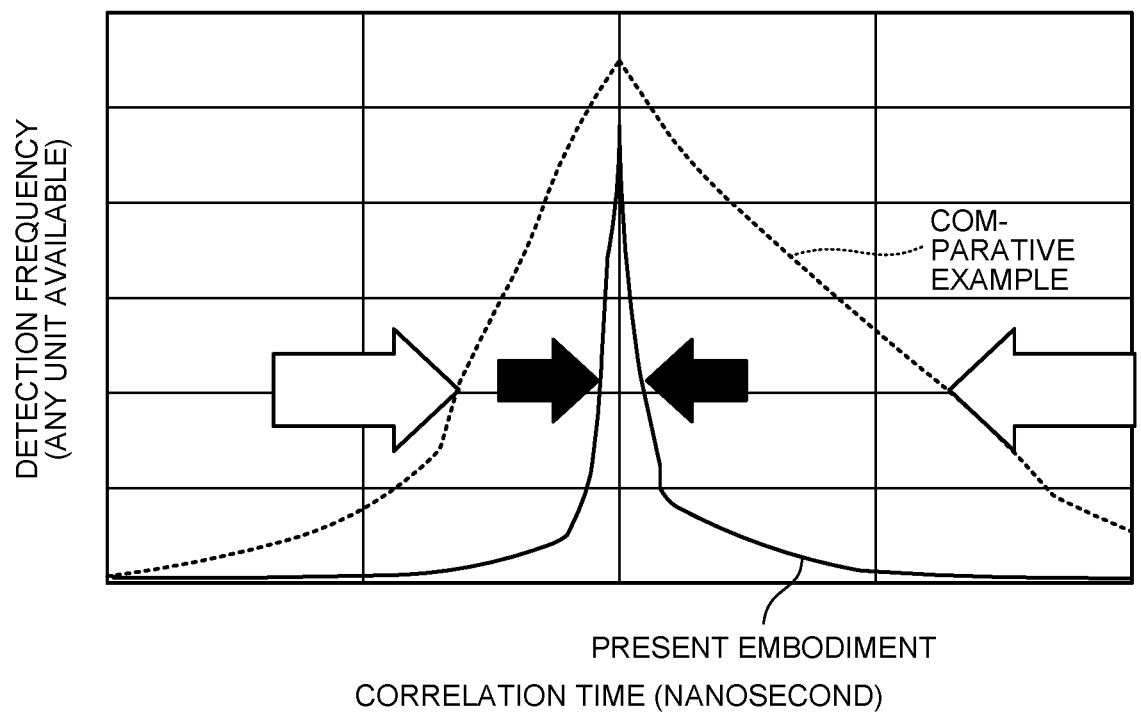
FIG. 9 is a diagram illustrating time-resolved spectra indicating correlation time with respect to detection frequency in connection with the comparative example and the first embodiment.

FIG. 9 is a diagram illustrating time-resolved spectra indicating correlation time with respect to detection frequency in connection with the comparative example and the present embodiment, the comparative example being an example where no curve fitting is performed. As illustrated in FIG. 9, the half-value width of the time-resolved spectrum of the output result by the data processing apparatus 1 according to the present embodiment is much smaller than the half-value width of the time-resolved spectrum in the comparative example. Therefore, as illustrated in FIG. 9, the data processing apparatus 1 according to the present embodiment can improve accuracy of estimation of the event occurrence time.

Second Embodiment

Explained in a second embodiment of the present invention is a Cherenkov TOFPET apparatus including the data processing apparatus 1 as explained in the first embodiment. The Cherenkov TOFPET apparatus including the data processing apparatus 1 may have any modality if the apparatus can detect Cherenkov light.

Figure 10:
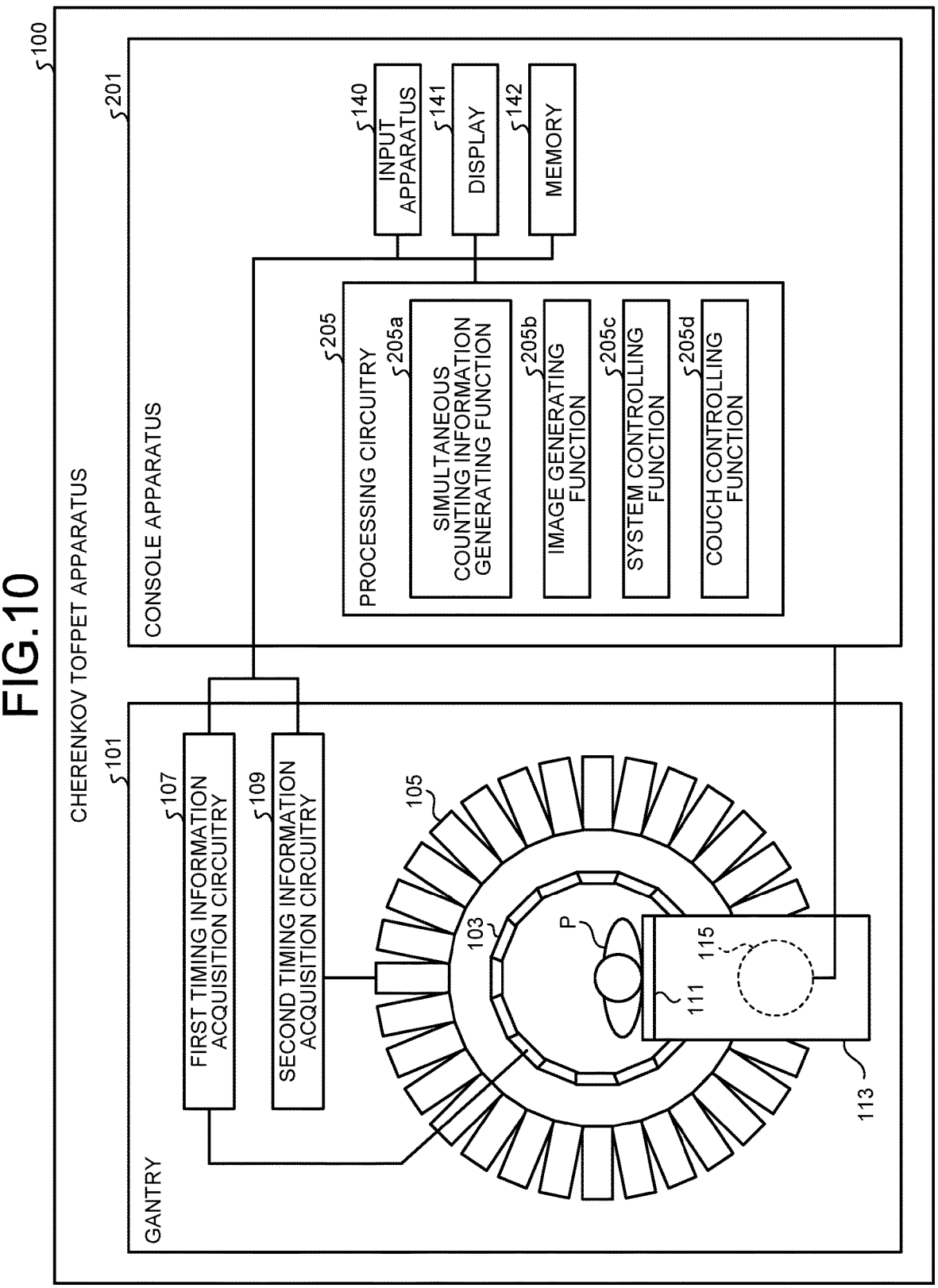
FIG. 10 is a schematic diagram illustrating an example of structure of a Cherenkov TOFPET apparatus according to a second embodiment of the present invention, the Cherenkov TOFPET apparatus equipped with the data processing apparatus according to the first embodiment.

FIG. 10 is a schematic diagram illustrating an example of structure of a Cherenkov TOFPET apparatus 100. As illustrated in FIG. 10, the Cherenkov TOFPET apparatus 100 includes a gantry 101 and a console apparatus 201.

The gantry 101 includes a first detector 103, a second detector 105, a first timing information acquisition circuitry 107, a second timing information acquisition circuitry 109, a couchtop 111, a couch 113, and a couch driving unit 115. The first detector 103 and the second detector 105 are arranged in a ring-like form to surround a subject P.

The first detector 103 detects Cherenkov light generated by a pair of gamma rays (hereinafter, "annihilation gamma rays") that is generated in a pair when positrons of the subject P and electrons annihilate. In other words, the first detector 103 is a detector for detecting gamma rays using Cherenkov light. The first detector 103 thereby acquires counting information concerning the annihilation gamma rays. The Cherenkov light generates in a time much shorter than the scintillation light, as indicated by the dotted-line frame of FIG. 4.

The first detector 103 is inferior to a detector of the pair annihilation gamma-rays using the scintillation light in terms of sensitivity to energy. However, detection of the gamma rays by the Cherenkov light is highly responsive to time, as indicated by the dotted-line frame of FIG. 4. Therefore, the first detector 103 is superior to the detector for detecting the scintillation light in terms of time resolution.

In other words, the first detector 103 has a characteristic of being advantageous in terms of time resolution over the second detector 105 that is configured to detect the scintillation light, while the second detector 105 that is configured to detect the scintillation light has a characteristic of being advantageous in terms of energy resolution over the first detector 103.

Therefore, the Cherenkov TOFPET apparatus 100 generates the counting information using the first detector 103 and the second detector 105. The Cherenkov TOFPET apparatus 100 thus generates the counting information, maintaining the high time resolution while keeping the energy resolution.

The first detector 103 includes the light emitter (radiator) 50 and the light sensor 51. The light emitter (radiator) 50 contains an atom with a large atomic number having a property of easily causing a photoelectric effect by the interaction with the incident radiation. Moreover, the light emitter 50 is implemented by a medium not easily generating the scintillation light; for example, BGO, and lead compounds such as lead glass, lead fluoride ($PbF_2$), and PWO ($PbWO_4$). In other words, the light emitter 50 of the first detector 103 is formed of a medium that easily causes the photoelectric effect but suppresses the scintillation due to the radiation, for example.

The light sensor 51 detects the Cherenkov light generated at the light emitter 50. The light sensor 51 is implemented by, for example, a SiPM that is an APD array and operates in a Geiger mode. In another example, the light sensor 51 is formed of a plurality of pixels that perform the photoelectric conversion, and each of the pixels is formed of a single photon avalanche diode (SPAD).

Note that the thickness of the light emitter 50 of the first detector 103 may be designed to be smaller than the thickness of a scintillator provided in the second detector 105, for example, in order to prevent the gamma-rays passing through the light emitter 50 from losing its entire energy. Thus, the annihilation gamma-rays enter the second detector 105 with most of the energy kept, while the Cherenkov light is generated in the first detector 103, and the scintillation light can be generated in the second detector 105.

The second detector 105 detects the scintillation light generated by the pair of gamma rays. The scintillation light is light (fluorescence) released again when electrons that has become excited by the interaction of the annihilation gamma-rays with the light emitter (scintillator) transits to the ground state again. The second detector 105 detects energy information of the annihilation gamma-rays released from the positrons in the subject P.

The second detector 105 faces a side of the first detector 103 that detects the Cherenkov light, the side being farther from the generation source of the annihilation gamma-rays released from the positrons in the subject P. In other words, the second detector 105 is a detector with a ring-like shape, which is similar to the first detector 103, and the diameter of the second detector 105 is larger than that of the first detector 103.

As illustrated in FIG. 4, the generation of the scintillation light is a slower process than the generation of the Cherenkov light. On the other hand, most part of the energy of the annihilation gamma-rays is converted into the scintillation light; therefore, from the viewpoint of measuring the energy of the annihilation gamma-rays, the second detector 105 using the scintillation light is advantageous over the first detector 103 using the Cherenkov light.

The second detector 105 is a photon counting type or Anger type detector, for example. The second detector 105 includes, for example, a scintillator operating as a light emitter, a light sensor, and a light guide. The thickness of the scintillator provided to the second detector 105 can be made larger than the thickness of the light emitter 50 provided to the first detector 103.

The scintillator converts the annihilation gamma-rays into the scintillation light. The scintillator is formed by, for example, scintillator crystal suitable for TOF measurement or energy measurement, such as LaBr3, LYSO, LSO, LGSO, or BGO, and is arranged two-dimensionally, for example.

The light sensor may be implemented by, for example, a SiPM as described above or a multiplier phototube. The multiplier phototube includes a photoelectric cathode that receives the scintillation light and generates photoelectrons, a multistage dynode that applies an electric field that accelerates the generated photoelectrons, and an anode corresponding to an outlet from which the electrons flow out. The multiplier phototube multiplies the scintillation light output from the scintillator and converts the scintillation light into electric signals.

The light guide is formed of a plastic material with the excellent light-transmitting property or the like, and sends the scintillation light output from the scintillator to the light sensor, for example the SiPM or the multiplier phototube.

The first timing information acquisition circuitry 107 converts the output signal of the first detector 103 into digital data and generates the counting information. This counting information includes a detection position and a detection time of the annihilation gamma-rays. The data processing apparatus 1 according to the first embodiment is incorporated into the first timing information acquisition circuitry 107. The above-mentioned detection time corresponds to the timing information $t_0$. The first timing information acquisition circuitry 107 specifies a plurality of light sensors that have converted the Cherenkov light into electric signals at the same timing. Then, the first timing information acquisition circuitry 107 calculates the position of center of gravity using the position of each of the specified light sensors and the intensity of the electric signal. Subsequently, the first timing information acquisition circuitry 107 specifies a detection element number (P) indicating the position of the light emitter 50 on which the annihilation gamma-rays have been incident.

The first timing information acquisition circuitry 107 specifies a detection time (T) when the first detector 103 has detected the Cherenkov light generated by the annihilation gamma-rays. Note that the detection time (T) may be either the absolute time or elapsed time since the start of the image capture. In this manner, the first timing information acquisition circuitry 107 generates the counting information including the detection element number (P) and the detection time (T).

The second timing information acquisition circuitry 109 generates the counting information from the output signal of the second detector 105, and stores the generated counting information in a memory 142 in the console apparatus 201. The second timing information acquisition circuitry 109 converts the output signal of the second detector 105 into digital data, and generates the counting information. This counting information includes the detection position, the energy value, and the detection time of the annihilation gamma-rays. For example, the second timing information acquisition circuitry 109 specifies a plurality of light sensors that have converted the scintillation light into electric signals at the same timing. Then, the second timing information acquisition circuitry 109 specifies a scintillator number (P) indicating the position of the scintillator on which the annihilation gamma-rays have been incident.

The data processing apparatus 1 according to the first embodiment is incorporated into the second timing information acquisition circuitry 109. The second timing information acquisition circuitry 109 specifies an energy value (E) of the annihilation gamma-rays incident into the second detector 105 by the integral calculation of the amplitude of the fitting function. In addition, the second timing information acquisition circuitry 109 specifies the timing information $t_0$ for the fitting function as the detection time (T) when the second detector 105 has detected the scintillation light generated by the annihilation gamma-rays. Note that the detection time (T) may be either the absolute time or elapsed time since the start of the image capture. In this manner, the second timing information acquisition circuitry 109 generates the counting information including the scintillator number (P), the energy value (E), and the detection time (T).

The first timing information acquisition circuitry 107 and the second timing information acquisition circuitry 109 may be implemented by, for example, a circuit of a CPU, a GPU, an ASIC, a programmable logic device, etc., or a processor.

When pileup occurs in the first detector 103 and the second detector 105, the specification circuitry 15 calculates the difference between the output signal and the fitting function. Then, the specification circuitry 15 performs curve fitting, using the fitting function, to waveform samples (pileup waveform) of a waveform DD that is generated by the difference. The determination on presence or absence of pileup corresponds to the determination of Yes at Step S208. In this situation, the specification circuitry 15 performs curve fitting to the pileup waveform after calculation of the difference.

Figure 11:
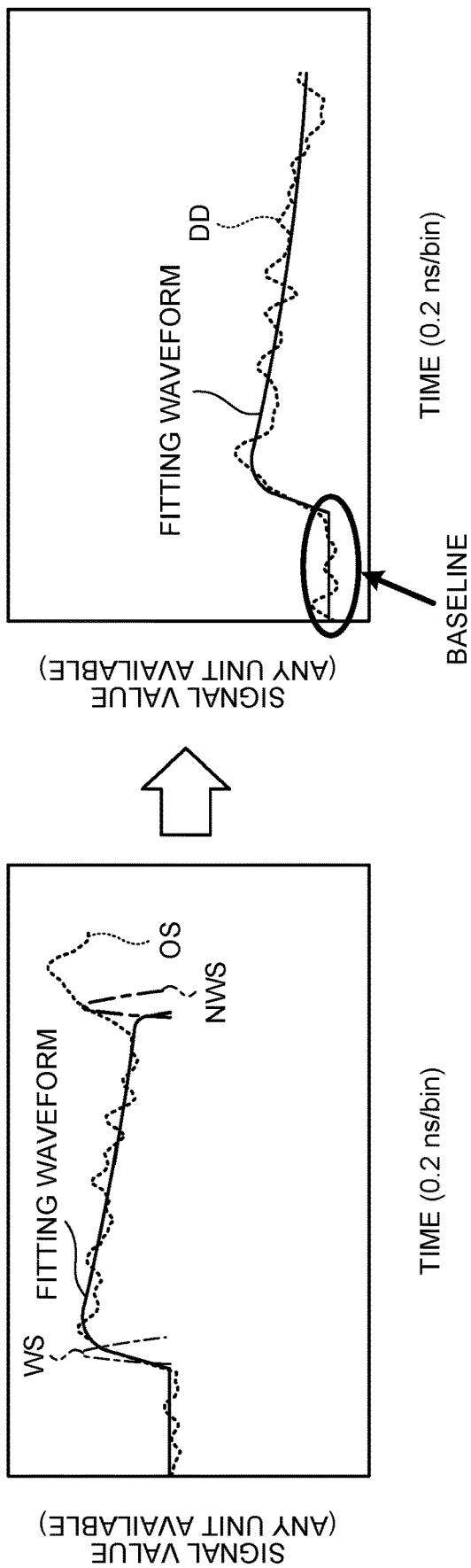
FIG. 11 is a diagram illustrating examples of an output signal, a shaped waveform, a new shaped waveform, and a fitting waveform in a timing acquiring process when a pileup occurs according to the second embodiment.

FIG. 11 is a diagram for illustrating examples of an output signal OS, the shaped waveform WS, a new shaped waveform NWS, and the fitting waveform in a timing acquiring process when a pileup occurs. As illustrated in FIG. 11, by using an event that the new shaped waveform NWS after the output of the shaped waveform WS exceeds the threshold Vref (hereinafter, "next gamma-ray exceedance time") as a trigger, the specification circuitry 15 performs curve fitting using the fitting function to the waveform samples WSR, which are obtained as samples by the next gamma-ray exceedance time.

In this curve-fitting, the specification circuitry 15 calculates the difference between the output signal OS and the fitting waveform. The specification circuitry 15 performs curve fitting, using the fitting function, to the waveform samples (pileup waveform) of the waveform DD that is generated by the difference. The specification circuitry 15 thereby further specifies the timing information, the gamma-ray's energy, and the contribution ($\beta$ in expression (1)) of the Cherenkov light to the detector signal for the pileup waveform, as well.

The couchtop 111 is a bed on which the subject P is placed, and is disposed on the couch 113. The couch driving unit 115 moves the couchtop 111 under control of a couch controlling function 205$d$ of processing circuitry 205. For example, the couch driving unit 115 moves the couchtop 111 so that the subject P moves into an image capturing port of the gantry 101.

The console apparatus 201 receives the operator's operation of the Cherenkov TOFPET apparatus 100 and controls capture of a PET image, and moreover reconfigures the PET image using the counting information collected by the gantry 101. As illustrated in FIG. 10, the console apparatus 201 includes the processing circuitry 205, an input apparatus 140, a display 141, and the memory 142. Note that the parts of the console apparatus 201 are connected to each other through a bus.

Respective processing functions performed by a simultaneous counting information generating function 205$a$, an image generating function 205$b$, a system controlling function 205$c$, and the couch controlling function 205$d$ are stored in the memory 142 in the format of computer programs that are executable by a processor. The processing circuitry 205 is a processor that reads out the computer program from the memory 142 and executes the computer program so as to achieve the function corresponding to the computer program. In other words, the processing circuitry 205 having read out the computer programs has the respective functions as illustrated inside the frame of the processing circuitry 205 in FIG. 10.

It is explained with reference to FIG. 10 that the processing functions performed by the simultaneous counting information generating function 205a, the image generating function 205b, the system controlling function 205c, and the couch controlling function 205d are achieved in one processing circuitry 205; however, the processing circuitry 205 may alternatively be configured by combining a plurality of independent processors and by executing the computer program in each processor, the processing circuitry 205 may achieve the functions. In other words, each of the aforementioned functions may be configured as the computer program and one processing circuitry 205 may execute each computer program. In another example, a particular function may be mounted in a dedicated independent computer program executing circuitry.

Note that in FIG. 10, the simultaneous counting information generating function 205a, the image generating function 205b, the system controlling function 205c, and the couch controlling function 205d are examples of a simultaneous counting information generating unit, an image generation unit, a system control unit, and a couch control unit, respectively. The term "processor" used in the above description refers to a circuit such as a CPU, a GPU, an ASIC, or a programmable logic device. The processor achieves the function by reading out and executing the computer program saved in the memory 142.

The processing circuitry 205 causes the simultaneous counting information generating function 205a to generate simultaneous counting information on the basis of the counting information about the first detector 103 that is acquired by the first timing information acquisition circuitry 107 and the counting information about the second detector 105 that is acquired by the second timing information acquisition circuitry 109, and stores the generated simultaneous counting information in the memory 142. The detailed process of the simultaneous counting information generating function 205a is described below.

the processing circuitry 205 causes the image generating function 205b to reconfigure the PET image. Specifically, the processing circuitry 205 causes the image generating function 205b to read out a time-series list of the simultaneous counting information stored in the memory 142, and reconfigures the PET image using the read time-series list. In addition, the processing circuitry 205 stores the reconfigured PET image in the memory 142.

The processing circuitry 205 causes the system controlling function 205c to control the gantry 101 and the console apparatus 201, thereby controlling the entire Cherenkov TOFPET apparatus 100. For example, the processing circuitry 205 causes the system controlling function unit 205c to control the image capture in the Cherenkov TOFPET apparatus 100.

The processing circuitry 205 causes the couch controlling function 205d to control the couch driving unit 115.

The input apparatus 140 is a mouse or a keyboard, for example, that is used to input various instructions or settings by the operator of the Cherenkov TOFPET apparatus 100, and transfers the input various instructions and settings to the processing circuitry 205. For example, the input apparatus 140 is used to input an image capture start instruction.

The display 141 is a monitor or the like that is referred to by the operator, and under control of the processing circuitry 205, displays a respiration waveform or a PET image of the subject, and displays a graphical user interface (GUI) for receiving various instructions or settings from the operator.

The memory 142 stores various pieces of data used in the Cherenkov TOFPET apparatus 100. The memory 142 is implemented by, for example, a semiconductor memory element such as a RAM or a flash memory, a hard disk, or an optical disk. The memory 142 stores therein, the counting information corresponding to the information in which the scintillator number (P), the energy value (E), and the detection time (T) are associated with each other, the simultaneous counting information in which the coincidence number corresponding to the serial number of the simultaneous counting information is associated with a set of counting information, the reconfigured PET image, and the like.

Explained below is a process of generating the simultaneous counting information in the Cherenkov TOFPET apparatus 100 according to the embodiment with reference to FIGS. 12 to 15.

Figure 12:
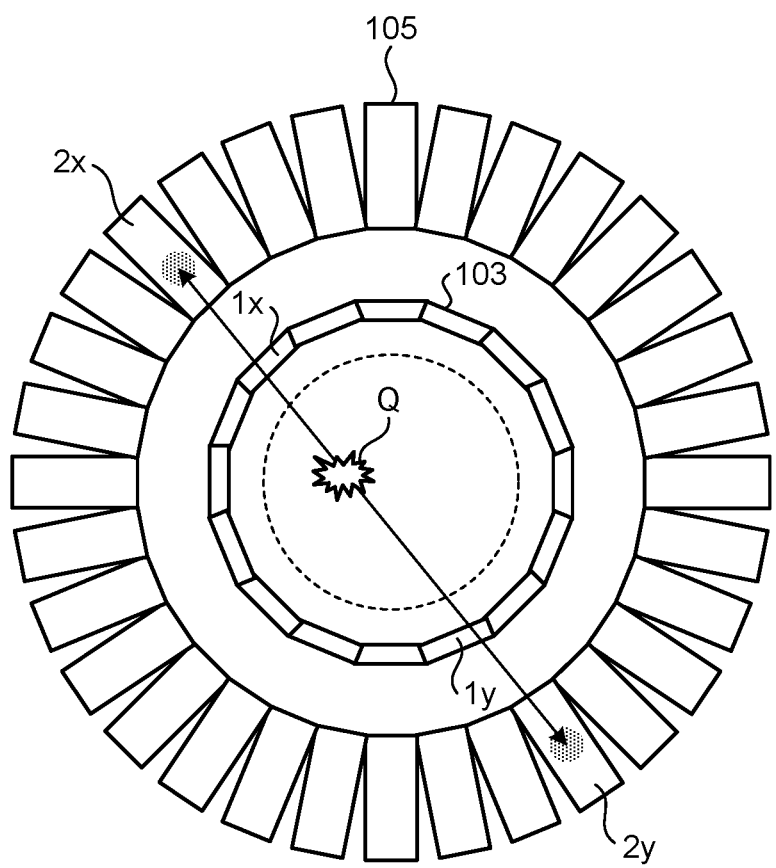
FIG. 12 is a diagram illustrating a counting process performed by the Cherenkov TOFPET apparatus according to the second embodiment.

As illustrated in FIG. 12, a case is explained where the Cherenkov light derived from a pair of gamma-rays produced as a pair from an annihilation point Q is detected by a pair of first detectors $1x$ and $1y$ and the scintillation light of a pair of gamma-rays produced as a pair from the annihilation point Q is detected by a pair of second detectors $2x$ and $2y$. In this case, the processing circuitry 205 causes the simultaneous counting information generating function 205a to generate the simultaneous counting information using data acquired by the pair of the first detectors and the pair of the second detectors.

Figure 13:
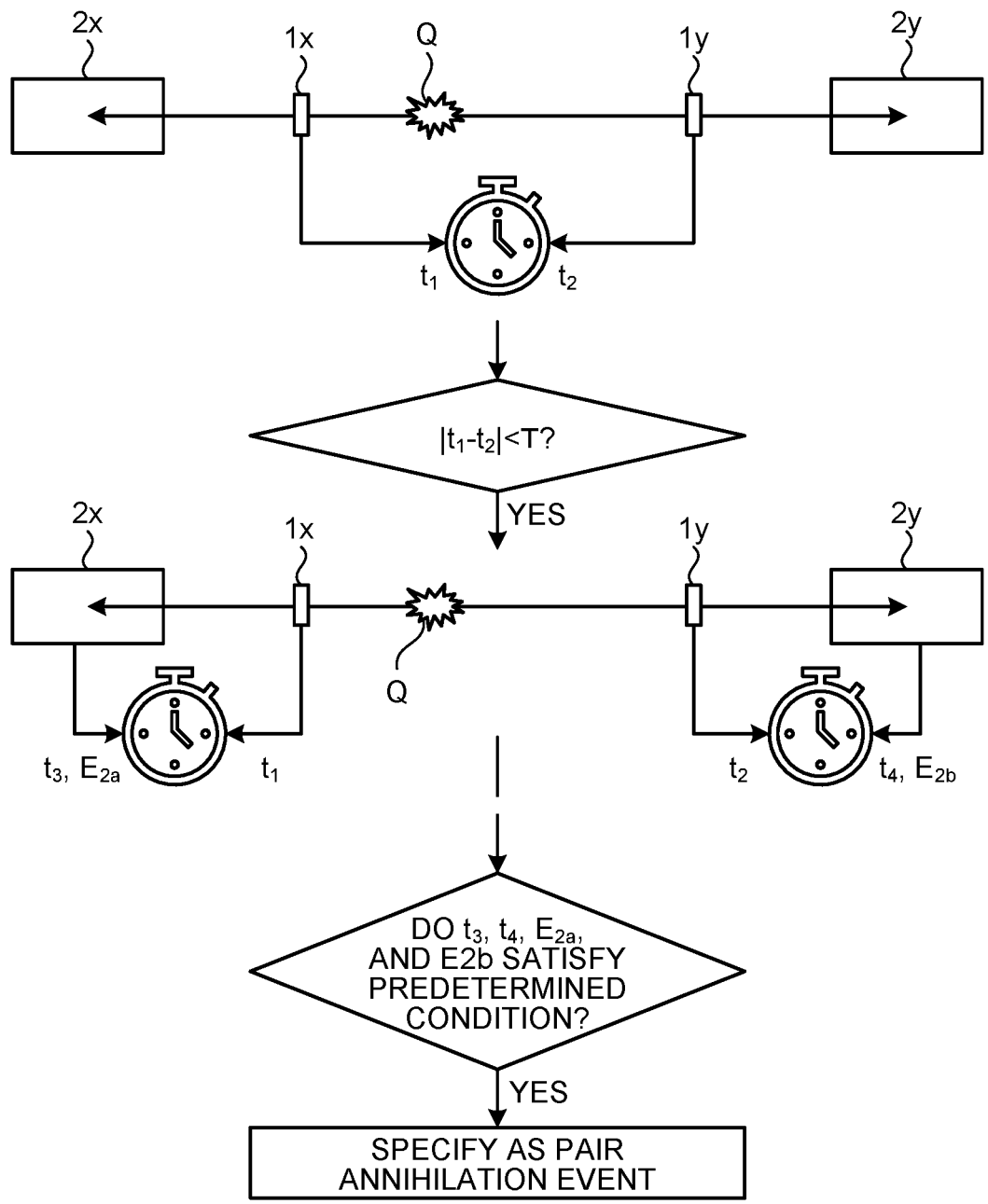
FIG. 13 is a diagram illustrating the counting process performed by the Cherenkov TOFPET apparatus according to the second embodiment.

There are two methods of generating the simultaneous counting information: one method as illustrated in FIG. 13 in which the simultaneous counting is performed in the first detector 103 and then, by referring to the data obtained in the second detector 105, the final simultaneous counting information is generated; and the other method in which the simultaneous counting is performed in the second detector 105 and then, by referring to the data obtained in the first detector 103, the final simultaneous counting information is generated. The former method will be explained using FIGS. 13 and 14, and the latter method will be explained using FIG. 15.

Figure 14:
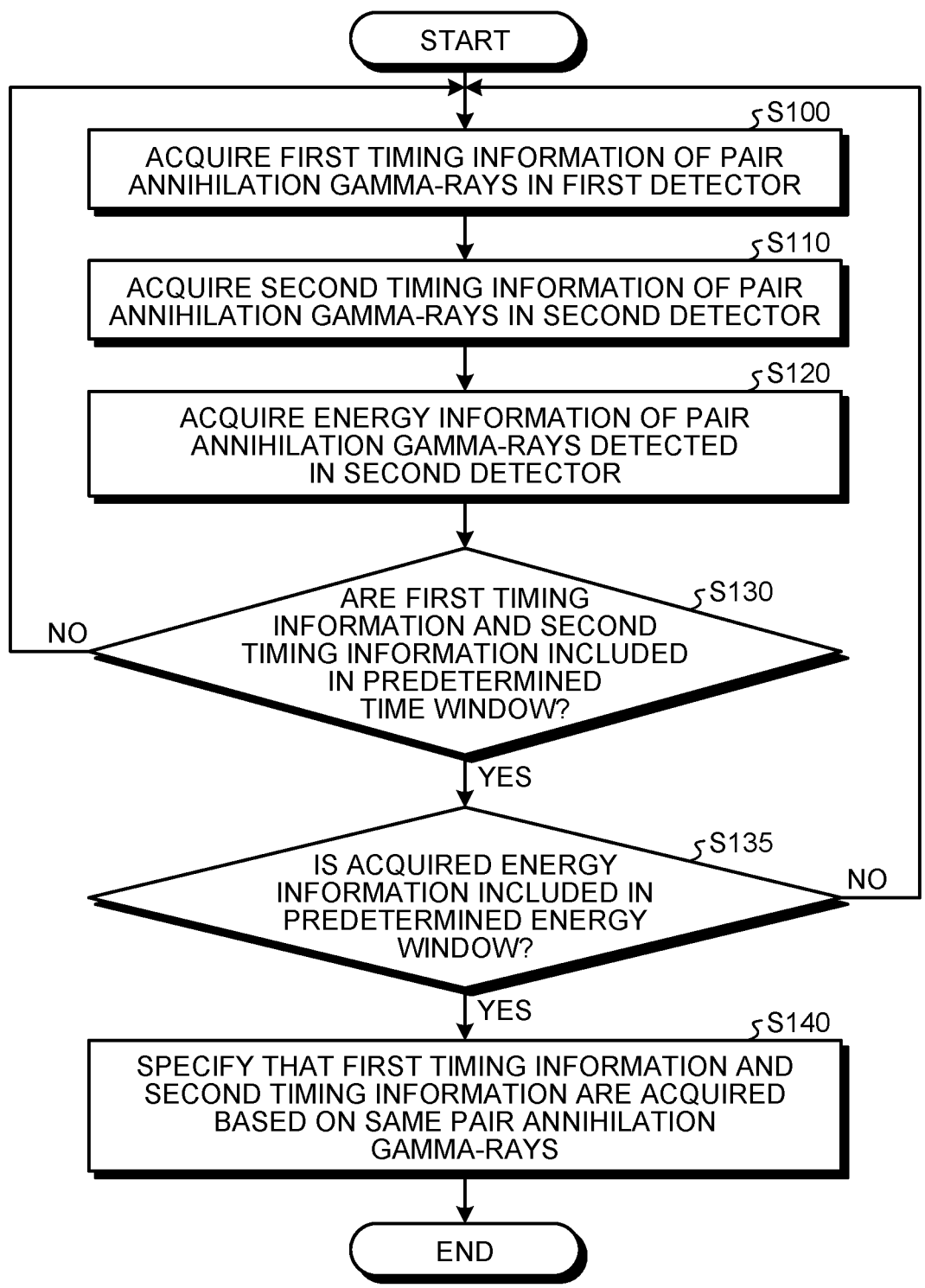
FIG. 14 is a flowchart illustrating a flow of processes performed by the Cherenkov TOFPET apparatus according to the second embodiment.

First, as the method of generating the simultaneous counting information, the method of performing the simultaneous counting in the first detector 103 first is described with reference to FIGS. 13 and 14. In this method, a process of generating the simultaneous counting information is performed using the data obtained from the first detector 103 with the better time resolution first. Specifically, as illustrated in FIG. 13, the processing circuitry 205 performs the process using the first detectors $1x$ and $1y$, and after that, performs the process using the second detectors $2x$ and $2y$, and specifies whether the event is the pair annihilation event and if it is the pair annihilation event, specifies the pair annihilation position and time. FIG. 14 is a flowchart illustrating an example of this processing procedure.

At step S100, the first timing information acquisition circuitry 107 acquires the first timing information of the pair annihilation gamma-rays in the first detector 103. In addition, the first timing information acquisition circuitry 107 transmits the acquired first timing information to the processing circuitry 205 in the console apparatus 201. Here, the first timing information of the pair annihilation gamma-rays in the first detector corresponds to, for example, a list of the detection element number (P) and the detection time (T).

As illustrated in FIG. 13, the first timing information acquisition circuitry 107 acquires a pair of pieces of first timing information of the pair annihilation gamma-rays from the first detector $1x$ that is in a certain direction and the first detector $1y$ that is on the approximately opposite side of the first detector $1x$. Thus, the processing circuitry 205 can cause the simultaneous counting information generating function 205a to estimate the generation position of the pair annihilation gamma-rays.

Explained below is a procedure of estimating the generation position of the pair annihilation gamma-rays from the pair of pieces of first timing information. The pair annihilation gamma-rays are released to the opposite sides due to the relation of momentum conservation along with the pair annihilation of positrons and electrons, and therefore, when Compton scattering or the like is ignored, the generation position of the pair annihilation gamma-rays exists on a line connecting the first detector 1x and the first detector 1y.

Next, when it is assumed that the distance between the first detector 1x and the generation position of the pair annihilation gamma-rays is $x_1$, the distance between the first detector 1y and the generation position of the pair annihilation gamma-rays is $y_1$, the detection time when the first detector 1x has observed the Cherenkov light is $t_1$, the detection time when the first detector 1y has observed the Cherenkov light is $t_2$, and the speed of light is c. The difference in detection time between the first detector 1x and the first detector 1y can be defined by the difference in time by which the light advances the difference of distance from the generation position. Thus, $x_1-y_1=c(t_1-t_2)$ is satisfied. In addition, the distance $L_1$ between the first detector 1x and the first detector 1y is known and the expression $x_1+y_1=L_2$ is satisfied.

By setting up the two expressions above simultaneously, it is possible to calculate the distance $x_1$ between the first detector 1x and the generation position of the pair annihilation gamma-rays, and the distance $y_1$ between the first detector 1y and the generation position of the pair annihilation gamma-rays. Therefore, the processing circuitry 205 can cause the simultaneous counting information generating function 205a to estimate the generation position and the generation time of the pair annihilation gamma-rays on the basis of the pair of pieces of timing information.

As is understood from the above expressions, when the generation position of the pair annihilation gamma-rays is near the center of the image capture range, the detection time is substantially the same in the first detector 1x and the first detector 1y. On the other hand, as the generation position of the pair annihilation gamma-rays is away from near the center of the image capture range, the difference in detection time between the first detector 1x and the first detector 1y increases. Therefore, the processing circuitry 205 can cause the simultaneous counting information generating function 205a to extract the event of the pair annihilation gamma-rays generated within a distance R from the center of the image capture range by extracting the pair annihilation gamma-rays generation event using a trigger that the difference in detection time between the first detector 1x and the first detector 1y is less than a threshold T.

In the process of extracting the pair annihilation gamma-rays event or the process of estimating the generation position of the pair annihilation gamma-rays in the simultaneous counting information generating function 205a of the processing circuitry 205, the response speeds of the detectors or variation among them may result in the occurrence of an error. However, it takes shorter after the Cherenkov light is generated from the interaction of the pair annihilation gamma-rays with the light emitter 50 and before the light sensor 51 detects the Cherenkov light in the first detector 103 configured to detect the Cherenkov light than in the second detector 105 configured to detect the scintillation light; therefore, the response speed of the first detector 103 is shorter and the extraction of the pair annihilation gamma-rays event and the estimation of the generation position of the pair annihilation gamma-rays are performed with high accuracy.

Subsequently, at step S110, the second timing information acquisition circuitry 109 acquires the second timing information of the pair annihilation gamma-rays in the second detector 105 in order to specify the event of the pair annihilation gamma-rays in which the first timing information is acquired on the basis of the first timing information acquired at step S100. The processing circuitry 205 causes the simultaneous counting information generating function 205a to generate the simultaneous counting information using both the first timing information acquired by the first detector 103 and the second timing information acquired by the second detector 105.

In addition, the second timing information acquisition circuitry 109 transmits the acquired second timing information to the processing circuitry 205 of the console apparatus 201. Here, the second timing information of the pair annihilation gamma-rays in the second detector is the counting information including the scintillator number (P) and the detection time (T), for example. In addition, the second timing information of the pair annihilation gamma-rays in the second detector 105 may be the counting information including the energy value (E) of the pair annihilation gamma-rays having entered the scintillator in addition to those above.

Note that at step S100 and step S110, the first timing information acquisition circuitry 107 and the second timing information acquisition circuitry 109 usually perform the processes at step S100 and step S110 at the same time in parallel instead of performing the processes sequentially.

Note that one example of the detection time (T) is the time when the second detector 105 has observed the scintillation light; however, the embodiment is not limited to this example. In another example, the detection time (T) may be the estimated time of the time when the Cherenkov light is generated by the interaction between the pair annihilation gamma-rays and the scintillator of the second detector 105, the estimated time being estimated based on the time when the second detector 105 has observed the scintillation light. In the second detector 105, the time when the pair annihilation gamma-rays are observed and the second detector 105 observes the scintillation light is a little delayed from the time when the pair annihilation gamma-rays interact with the scintillator of the second detector 105 and the excited state is generated. As described above, the detection time (T) may be either the absolute time or elapsed time since the start of the image capture.

Back to FIG. 13, the second timing information acquisition circuitry 109 acquires a pair of pieces of second timing information about the pair annihilation gamma-rays from the second detector 2x and the second detector 2y on the side substantially opposite to the second detector 2x. Thus, in a manner similar to the case of the first detector 103, the processing circuitry 205 can cause the simultaneous counting information generating function 205a to estimate the generation position of the pair annihilation gamma-rays.

That is to say, it is assumed that the distance between the second detector 2x and the generation position of the pair annihilation gamma-rays is $x_2$, the distance between the second detector 2y and the generation position of the pair annihilation gamma-rays is $y_2$, the detection time when the second detector 2x has observed the scintillation light is $t_3$, the detection time when the second detector 2y has observed the scintillation light is $t_4$, and the speed of light is c. Herein, the difference in detection time between the second detector 2x and the second detector 2y can be defined by the difference in time by which the light advances the difference of distance from the generation position. Thus, $x_2-y_2=c(t_3-$ $t_4$) is satisfied. In addition, the distance $L_2$ between the second detector $2x$ and the second detector $2y$ is known and the expression $x_2+y_2=L_2$ is satisfied.

By setting up the two expressions above simultaneously, it is possible to calculate the distance $x_2$ between the second detector $2x$ and the generation position of the pair annihilation gamma-rays, and the distance $y_2$ between the second detector $2y$ and the generation position of the pair annihilation gamma-rays. Therefore, the processing circuitry 205 can cause the simultaneous counting information generating function 205a to estimate the generation position and the generation time of the pair annihilation gamma-rays on the basis of the pair of pieces of timing information.

As is understood from the above expressions, when the generation position of the pair annihilation gamma-rays is near the center of the image capture range, the detection time is substantially the same in the second detector $2x$ and the second detector $2y$. On the other hand, as the generation position of the pair annihilation gamma-rays is away from near the center of the image capture range, the difference in detection time between the second detector $2x$ and the second detector $2y$ increases. Therefore, the processing circuitry 205 can cause the simultaneous counting information generating function 205a to extract the event of the pair annihilation gamma-rays generated within the distance R from the center of the image capture range by extracting the pair annihilation gamma-rays generation event using the trigger that the difference in detection time between the second detector $2x$ and the second detector $2y$ is less than the threshold T.

In the process of extracting the pair annihilation gamma-rays event or the process of estimating the generation position of the pair annihilation gamma-rays in the simultaneous counting information generating function 205a of the processing circuitry 205, the response speed of the detector or the variation thereof results in the occurrence of an error. Here, in the second detector 105, it takes relatively long after the scintillation light is generated by the interaction of the pair annihilation gamma-rays with the scintillator and before the second detector 105 detects the generated scintillation light.

However, in the second detector 105, after the pair annihilation gamma-rays interact with the scintillator by the photoelectric effect and before the system returns to the ground state, most part of the energy of the pair annihilation gamma-rays is released again as the scintillation light. Therefore, by counting the number of scintillation light released again, the second timing information acquisition circuitry 109 can acquire the information about the energy of the pair annihilation gamma-rays. At step S120, the second timing information acquisition circuitry 109 further acquires the energy information of the pair annihilation gamma-rays detected in the second detector 105.

The energy of the pair annihilation gamma-rays is 511 keV, which is a predetermined energy corresponding to the rest mass of the positron. Therefore, if the energy of the observed gamma-rays is largely deviated from the predetermined energy, the observed gamma-rays are the gamma-rays generated due to Compton scattering or the like. Therefore, the processing circuitry 205 can cause the simultaneous counting information generating function 205a to eliminate the scattering event such as Compton scattering using the energy information of the observed gamma-rays.

Subsequently, at step S130, the processing circuitry 205 causes the simultaneous counting information generating function 205a to determine whether the first timing information and the second timing information are included in a predetermined time window. The simultaneous counting information generating function 205a thereby determines whether the first timing information and the second timing information are about the same pair annihilation gamma-rays.

Here, in the case where the first timing information and the second timing information are included in the predetermined window, the processing circuitry 205 causes the simultaneous counting information generating function 205a to specify that the first timing information and the second timing information are the timing information acquired based on the same pair annihilation gamma-rays and the process advances to step S135.

In one example, in the case where the difference between the generation time of the pair annihilation gamma-rays that is calculated based on the first timing information acquired at step S100 and the generation time of the pair annihilation gamma-rays that is calculated based on the second timing information acquired at step S110 is less than a predetermined threshold and is included in a predetermined time window, the processing circuitry 205 causes the simultaneous counting information generating function 205a to specify that the first timing information and the second timing information are acquired based on the same pair annihilation gamma-rays.

Furthermore, only in the case where the difference between the generation position of the pair annihilation gamma-rays that is calculated based on the first timing information acquired at step S100 and the generation position of the pair annihilation gamma-rays that is calculated based on the second timing information acquired at step S110 is less than the predetermined threshold, the processing circuitry 205 may cause the simultaneous counting information generating function 205a to specify that the first timing information and the second timing information are acquired based on the same pair annihilation gamma-rays.

In another example, as illustrated in FIG. 13, in the case where the difference between the detection time in the first detector 103 and the detection time in the second detector 105 is included in a predetermined time window, the processing circuitry 205 causes the simultaneous counting information generating function 205a to specify that the first timing information and the second timing information are the timing information acquired based on the same pair annihilation gamma-rays. For example, in FIG. 13, in a case where the distance between the first detector $1x$ and the second detector $2x$ is L, the difference $t_3-t_1$ between the detection time $t_1$ in the first detector $1x$ and the detection time $t_3$ in the second detector $2x$ is about L/c, in which c is the speed of light.

Therefore, in a case where the difference between the difference $t_3-t_1$ between the detection time in the first detector 103 and the detection time in the second detector 105 and the time L/c estimated from the distance between the detectors are included in a predetermined time window, the processing circuitry 205 causes the simultaneous counting information generating function 205a to specify that the first timing information and the second timing information are the timing information acquired based on the same pair annihilation gamma-rays.

Subsequently, at step S135, the processing circuitry 205 causes the simultaneous counting information generating function 205a to determine whether the acquired energy information is included in the predetermined energy window. Here, the energy of the pair annihilation gamma-rays is always 511 keV regardless of the nuclide at the time of generation. Therefore, in a case where the energy of the observed gamma-rays is much lower than 511 keV, it is possible to determine that the observed gamma-rays are influenced by Compton scattering or the like.

Therefore, by determining whether the acquired energy information is included in the predetermined energy window, the processing circuitry 205 can cause the simultaneous counting information generating function 205a to exclude the data influenced by the scattering from the object to be reconfigured.

For example, the processing circuitry 205 can cause the simultaneous counting information generating function 205a to determine whether the difference between the estimated energy of the pair annihilation gamma-rays detected in the second detector 105 at step S120 and 511 keV, which is the energy when the pair annihilation gamma-rays are generated, is less than the predetermined threshold and is included in the predetermined energy window.

If the acquired energy information is included in the predetermined energy window (Yes at step S135), the process advances to step S140 and the processing circuitry 205 causes the simultaneous counting information generating function 205a to specify that the first timing information and the second timing information are acquired based on the same pair annihilation gamma-rays. On the other hand, if the acquired energy information is not included in the predetermined energy window (No at step S135), the processing circuitry 205 causes the simultaneous counting information generating function 205a to determine that the data is influenced by scattering, for example, and excludes this data from the object to be reconfigured.

Figure 15:
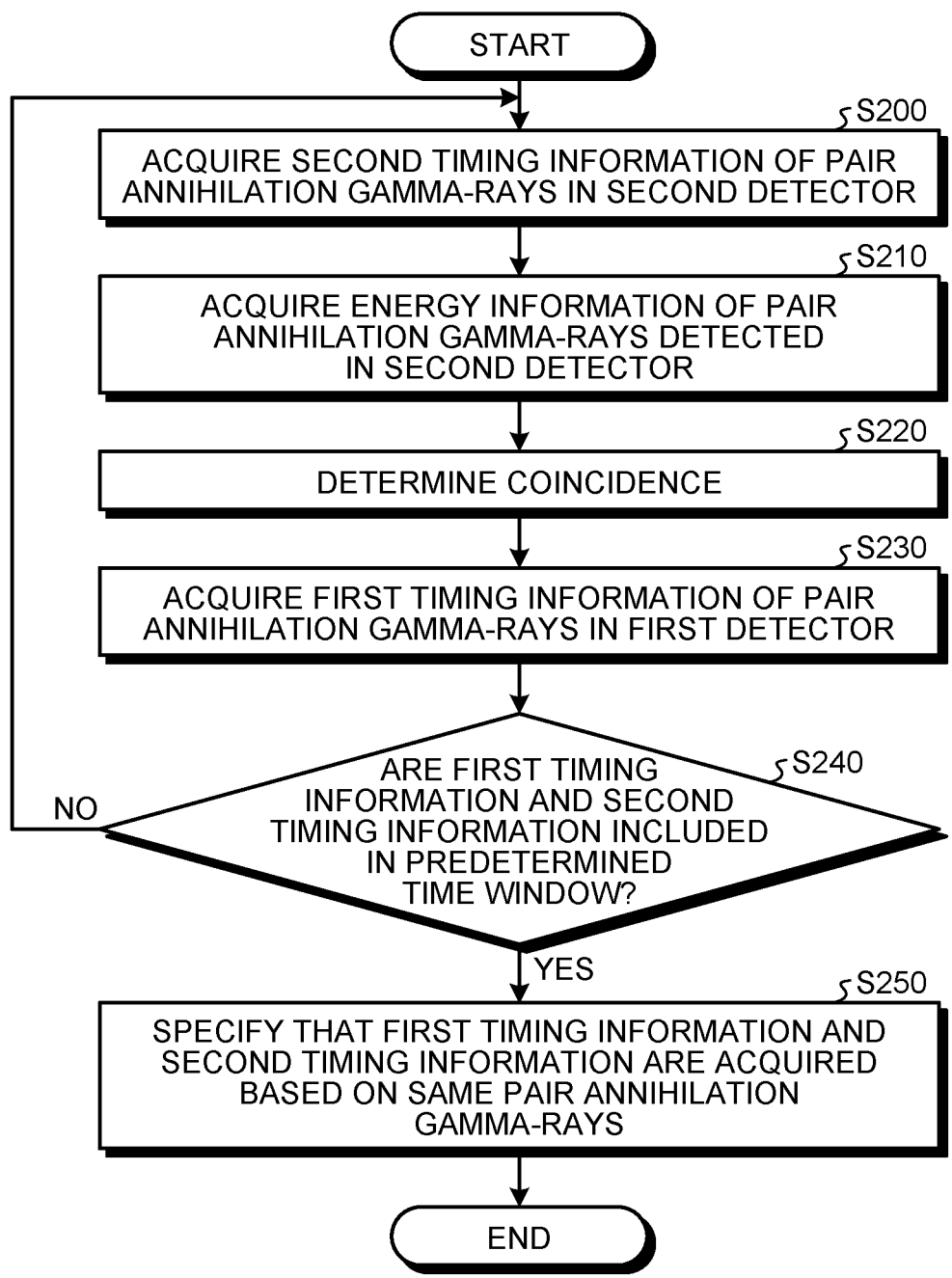
FIG. 15 is a flowchart illustrating a flow of processes performed by the Cherenkov TOFPET apparatus according to the second embodiment.

Subsequently, with reference to FIG. 15, description is made of a case in which the processing circuitry 205 causes the simultaneous counting information generating function 205a to determine the coincidence using the second timing information first, and then generate the final counting information using the first timing information. The process in FIG. 15 is similar to that in FIG. 14 but the order of steps is different. The process common to that in FIG. 14 is not described below. In FIG. 14 and FIG. 15, the contents of the final process are substantially the same but the order of steps is different, so that the time required in the calculating process may be different, for example. Therefore, whether the process in FIG. 14 is used or the process in FIG. 15 is used is selected depending on the number of events in the first detector 103 and the second detector 105 or the number of scattering events, for example.

First, at step S200, the second timing information acquisition circuitry 109 acquires the second timing information of the pair annihilation gamma-rays in the second detector 105. At step S210, the second timing information acquisition circuitry 109 further acquires the energy information of the pair annihilation gamma-rays detected in the second detector 105. The processes at step S200 and S210 are similar to the processes at S110 and S120 in FIG. 14.

Subsequently, at step S220, the processing circuitry 205 causes the simultaneous counting information generating function 205a to determine the coincidence on the basis of the energy information of the pair annihilation gamma-rays detected in the second detector 105. For example, the processing circuitry 205 causes the simultaneous counting information generating function 205a to determine whether the acquired energy information is included in a predetermined energy window, in a manner similar to the process at step S135. In another example, the processing circuitry 205 causes the simultaneous counting information generating function 205a to determine whether the difference between the estimated energy of the pair annihilation gamma-rays detected in the second detector and 511 keV, which is the energy when the pair annihilation gamma-rays are generated is less than the predetermined threshold and is included in the predetermined energy window. The processing circuitry 205 determines that the data not included in the predetermined energy window is the data influenced by the scattering and excludes such data from the object to be reconfigured.

On the other hand, if the acquired energy information is included in the predetermined energy window, the processing circuitry 205 causes the simultaneous counting information generating function 205a to estimate the generation position and the generation time of the pair annihilation gamma-rays on the basis of the scintillator number (P) and the detection time (T) using the procedure described above with reference to FIG. 14, for example. In addition, for example, the processing circuitry 205 causes the simultaneous counting information generating function 205a to extract, as the simultaneous counting information, the event of the pair annihilation gamma-rays generated within the distance R from the center of the image capture range by extracting the pair annihilation gamma-rays generation event using the trigger that the difference in detection time between the opposite detectors in the second detector 105 is less than the threshold T.

Subsequently, the first timing information acquisition circuitry 107 acquires the first timing information of the pair annihilation gamma-rays in the first detector 103 at step S230. In addition, the first timing information acquisition circuitry 107 transmits the acquired first timing information to the processing circuitry 205 in the console apparatus 201. Here, the first timing information of the pair annihilation gamma-rays in the first detector 103 is, for example, the detection element number (P) and the detection time (T). The process at step S230 is similar to the process at step S100 in FIG. 14.

Subsequently, at step S240, the processing circuitry 205 causes the simultaneous counting information generating function 205a to determine whether the first timing information and the second timing information are included in the predetermined time window, and in a case where the first timing information that is the timing information in the first detector 103 and the timing information in the second detector 105 are included in the predetermined time window (Yes at step S240), the process advances to step S250. At this step, the simultaneous counting information generating function 205a specifies that the first timing information that is the timing information in the first detector 103 and the second timing information that is the timing information in the second detector 105 have been acquired based on the same pair annihilation gamma-rays. Note that the process at step S240 is similar to the process at step S130.

In this manner, the processing circuitry 205 causes the simultaneous counting information generating function 205a to specify the timing information in the first detector 103 corresponding to the event of the pair annihilation gamma-rays detected in the second detector 105 on the basis of the determined coincidence. In this manner, the processing circuitry 205 causes the simultaneous counting information generating function 205a to generate the simultaneous counting information using the first timing information in the first detector 103 and the second timing information in the second detector 105. Here, the simultaneous counting information is the information containing the time and position where the pair annihilation gamma-rays are generated, for example. The processing circuitry 205 causes the image generating function 205b to generate the PET image on the basis of this simultaneous counting information.

As described above, the Cherenkov TOFPET apparatus 100 according to the second embodiment acquires the detector signal containing the first component that is based on the Cherenkov light and the second component that is based on the scintillation light, and it specifies the timing information about generation of the detector signal by curve fitting to the first component. The Cherenkov TOFPET apparatus 100 thus obtains the same effect as the first embodiment.

Moreover, even when a pileup occurs as illustrated in FIG. 11, the Cherenkov TOFPET apparatus 100 can perform curve fitting to the pileup waveform by calculating the difference between the output signal and the fitting function. With this configuration, the Cherenkov TOFPET apparatus 100 can specify the correct timing information even when a pileup occurs. This enables easy execution of pileup correction even when a waveform derived from another gamma ray overlaps with the output signal, i.e., even when a pileup occurs.

Furthermore, this Cherenkov TOFPET apparatus 100 can specify likely timing information and an amplitude (crest value) of the detector signal even when a circuit noise overlaps with the detector signal. This can narrow the spectrum of the number of counts with respect to the crest value and improve the signal-to-noise (S/N) ratio in the PET image.

Figure 16:
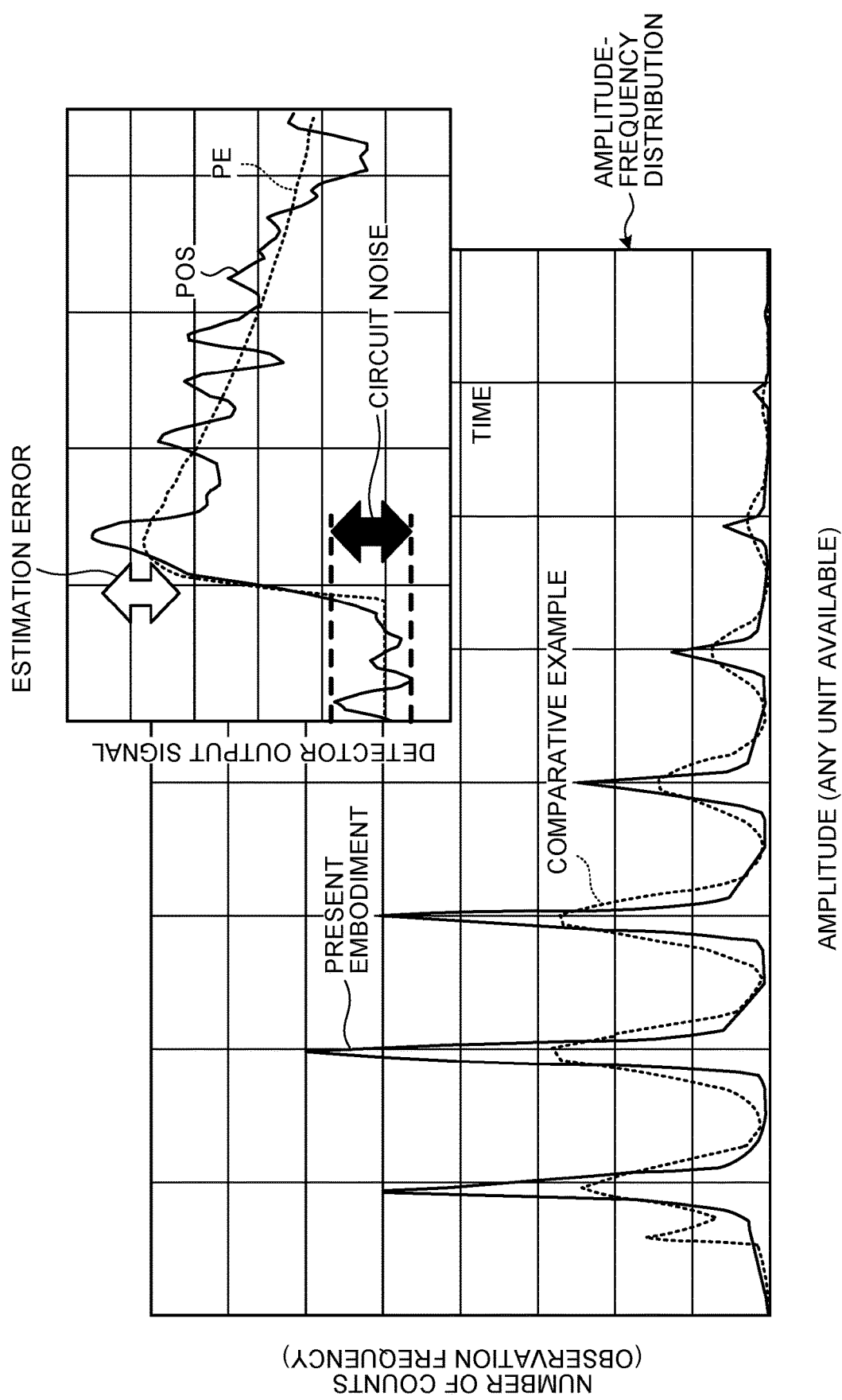
FIG. 16 is a diagram including a graph illustrating a distribution (amplitude-frequency distribution) of the number of counts (observation frequencies) with respect to amplitude (crest value) in connection with the comparative example and the second embodiment and a graph illustrating estimation error in the amplitude in connection with the comparative example.

FIG. 16 is a diagram including a graph illustrating a distribution (amplitude-frequency distribution) of the number of counts (observation frequencies) with respect to amplitude (crest value) in connection with the comparative example and the present embodiment and a graph illustrating estimation error in the amplitude in connection with the comparative example, the comparative example being an example where no curve fitting is performed. The magnitude of the amplitude depends on the number of photons observed. As seen from the graph illustrating the estimation error in the amplitude of FIG. 16, for amplitude PE of the comparative example, it fails to accurately estimate the amplitude for an output signal POS due to influence of circuit noises caused by transmission lines, heat, etc. In other words, the amplitude estimated in the comparative example is less than the actual output signal POS because of presence of the estimation error caused by circuit noises.

Therefore, in the amplitude-frequency distribution as illustrated in FIG. 16, the present embodiment has larger numbers of counts with narrower half-value widths than the comparative example. These indicate that the amplitude-frequency distribution according to the present embodiment has a sharpen spectrum of the number of photons with respect to the crest value, that is, the present embodiment can estimate the number of photons more accurate than the comparative example by reducing the estimation error of in the crest value and improve the S/N ratio in the PET image.

Furthermore, the present embodiment does not need a TDC with a high time resolution, and it needs neither calibration for each detector that relates to improvement of the trigger-time-walk, i.e., each of a plurality of pixels nor a large memory capacity required for learning. Due to these, the present embodiment can achieve improvement of the trigger-time-walk, pile correction, and improvement of the S/N ratio simply and easily and even at low cost.

Applications

The present application relates to an application of the first embodiment, relating to setting of an initial value of β in expression (1), etc. It has been known that the number of Cherenkov photons N, which is generated when γ rays impart energy $E_{dep}$ in a radiator provided, is given by expression (3) as follow in accordance with the Frank-Tamm formula:

$$\frac{dN}{dE_{dep}} = 2A\pi\alpha Z^2 \left(\frac{1}{\lambda_1} - \frac{1}{\lambda_2}\right)\left(1 - \frac{1}{\beta^2 n^2}\right) \quad (3)$$

where, in the right side of expression (3) above, A is a proportionality coefficient representing stopping power of the γ rays, α is a fine structure constant (1/137), Z is an electric charge of charged particles that cause Cherenkov radiation, $\lambda_1$ and $\lambda_2$ are both ends of a visible-light wavelength of the Cherenkov radiation, and n is a refractive index of a medium.

Figure 17:
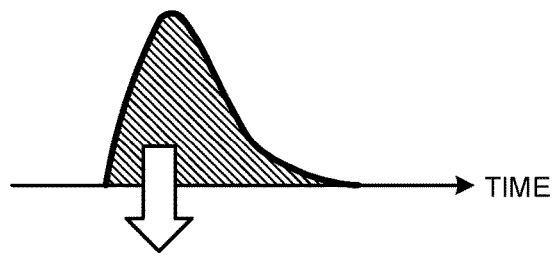
FIG. 17 is a diagram illustrating an example of energy $E_{dep}$, according to an application of the first embodiment.

FIG. 17 is a diagram illustrating an example of the energy $E_{dep}$. As illustrated in FIG. 17, the area of pulses that are generated by incidence of gamma rays on a radiator, such as a scintillator, in other words, the sum of the A/D converted values or the like corresponds to the observation energy of the gamma rays. The observation energy roughly corresponds to the energy $E_{dep}$ imparted to the radiator, such as a scintillator.

Parameter β in the right side of expression (3) is a speed relative to the photon speed in a vacuum of charged particles included in a material, and it is defined by expression (4) as follow:

$$\beta = \sqrt{1 - \left(\frac{1}{\frac{E_{dep}}{m_0 c^2} + 1}\right)^2} \quad (4)$$

where, in the right side of expression (4), $m_0$ is a rest mass of electrons and c is the speed of light. The dependency of the number of Cherenkov photons N to the detector observation energy ($E_{dep}$) can be found from usage of expressions (3) and (4). It is found from expression (3) that a condition to generate the Cherenkov light is β×n>1, energy satisfying β=1/n is a threshold energy $E_{th}$ as illustrated in FIG. 17, and the Cherenkov light generates when $E_{dep} \geq E_{th}$.

It is difficult to analytically solve a differential expression concerning N, which is obtained by substituting expression (4) to expression (3); however, it is possible to numerically solve the differential expression. An approach using no numerical solution includes approximation by a straight line having the threshold energy $E_{th}$ as an intercept, for example. The straight line is given by expression (5) as follow, for example:

$$N(E_{dep}) = \begin{cases} 0 & \text{for } E_{dep} < E_{th} \\ \gamma(E_{dep} - E_{th}) & \text{for } E_{dep} \geq E_{th} \end{cases} \quad (5)$$

Figure 18:
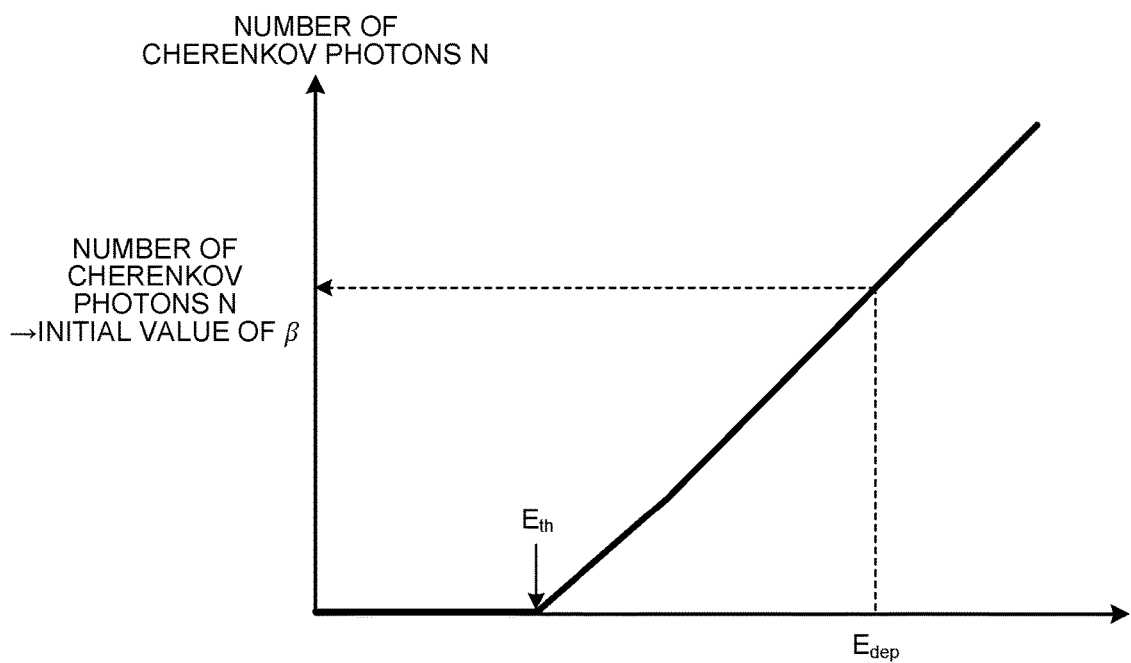
FIG. 18 is a diagram illustrating dependency of number of Cherenkov-light photons N with respect to observation γ-ray energy in expression (5), which is an application example of the first embodiment.

FIG. 18 is a diagram illustrating the dependency of the number of Cherenkov photons N with respect to the observation γ-ray energy in connection with expression (5). Expression (5) indicates, as illustrated in FIG. 18, that the number of Cherenkov photons N can be predicted roughly by knowing rough energy that incident γ rays imparted to the radiator. By using this nature, the specification circuitry 15 performs integration of the observation pulses as illustrated in FIG. 17 to measure the rough imparted energy. The specification circuitry 15 determines whether the observation energy is equal to or greater than the threshold energy $E_{th}$, and when the observation energy is equal to or greater than the threshold energy $E_{th}$, estimates the number of Cherenkov photons N and sets the initial value of β in expression (1). The specification circuitry 15 evaluates the entire of the pulses with expression (3) again. With these, the application example of the first embodiment can improve the accuracy in estimating the observation time $t_0$.

If the technical ideas in the embodiments are realized with a data processing method, the data processing method includes: acquiring a detector signal containing a first component that is based on Cherenkov light and a second component that is based on scintillation light; and specifying timing information about generation of the detector signal by curve fitting to the first component. The effects of the data processing method are the same as the embodiments, and their explanation is not repeated.

If the technical ideas in the embodiments are realized with a data processing program, the data processing program causes a computer to: acquire a detector signal containing that is based on Cherenkov light and a second component that is based on scintillation light; and specify timing information about generation of the detector signal by curve fitting to the first component.

The timing acquiring process can also be achieved by installing the data processing program to a computer for a Cherenkov TOFPET apparatus, a data processing server, etc., and loading it on a memory. The program herein that can cause the computer to perform the timing acquiring process can be distributed such that the program is stored in a storage medium, such as a magnetic disk (hard disk, etc.), an optical disk (CD-ROM, DVD, etc.) or a semiconductor memory. The processing procedures and effects of the data processing program are the same as the first embodiment or the second embodiment, and their explanation is not repeated.

According to at least one of the embodiments described above, the accuracy in estimating an event occurrence time can be improved in a simply manner and with a low cost.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A data processing apparatus comprising:
   acquisition circuitry configured to acquire a detector signal containing a first component that is based on Cherenkov light and a second component that is based on scintillation light; and
   specification circuitry configured to specify timing information about generation of the detector signal by curve fitting to the first component, wherein
   the specification circuitry is configured to specify the timing information by curve fitting to the first component and the second component.

2. The data processing apparatus according to claim 1, wherein
   the specification circuitry is configured to specify as the timing information an arrival time when gamma rays from which the Cherenkov light is generated arrive at a detector.

3. The data processing apparatus according to claim 2, wherein
   the specification circuitry is further configured to specify energy of the gamma rays by the curve fitting.

4. The data processing apparatus according to claim 1, wherein
   the specification circuitry is configured to perform the curve fitting using an analytic function indicating temporal change in the detector signal caused by the Cherenkov light and the scintillation light, and
   the function has an amplitude of the detector signal and the timing information as parameters about the curve fitting.

5. The data processing apparatus according to claim 4, wherein
   the function further has a parameter about a contribution of the Cherenkov light to the detector signal, and
   the specification circuitry is configured to specify the parameter about the contribution by the curve fitting.

6. A data processing apparatus comprising:
   a divider that divides an output waveform that is output from a light sensor into a first output waveform and a second output waveform;
   waveform shaping circuitry configured to shape the first output waveform;
   a comparator configured to compare the shaped first output waveform to a predetermined threshold value;
   determination circuitry configured to determine necessity of sampling of the second output waveform based on an output from the comparator;
   a convertor configured to convert the second output waveform to a digital waveform based on a result of determination by the determination circuitry; and
   specification circuitry configured to specify timing information about generation of the output waveform by curve fitting to the digital waveform.

7. A data processing method comprising:
   acquiring a detector signal containing a first component that is based on Cherenkov light and a second component that is based on scintillation light; and
   specifying timing information about generation of the detector signal by curve fitting to the first component, including specifying the timing information by curve fitting to the first component and the second component.

8. A non-transitory computer-readable storage medium for storing a data processing program that causes a computer to execute:
   acquiring a detector signal containing a first component that is based on Cherenkov light and a second component that is based on scintillation light; and
   specifying timing information about generation of the detector signal by curve fitting to the first component, including specifying the timing information by curve fitting to the first component and the second component.

* * * * *